United States Patent [19]
Buchin

[11] Patent Number: 5,589,874
[45] Date of Patent: Dec. 31, 1996

[54] VIDEO IMAGING SYSTEM WITH EXTERNAL AREA PROCESSING OPTIMIZED FOR SMALL-DIAMETER ENDOSCOPES

[75] Inventor: Michael P. Buchin, Palo Alto, Calif.

[73] Assignee: Origin Medsystems, Inc., Menlo Park, Calif.

[21] Appl. No.: 434,207

[22] Filed: May 4, 1995

Related U.S. Application Data

[63] Continuation of Ser. No. 74,110, Jun. 9, 1993, abandoned.

[51] Int. Cl.$^6$ ...................................................... H04N 7/18
[52] U.S. Cl. .................. 348/72; 348/71; 348/65; 348/588
[58] Field of Search .......................... 348/65, 72, 70, 348/588, 597, 586; 128/10, 6

[56] References Cited

U.S. PATENT DOCUMENTS

| | | | |
|---|---|---|---|
| 4,571,619 | 2/1986 | Mewitz | 348/586 |
| 4,891,695 | 2/1990 | Uchikubo et al. | 348/72 |
| 4,977,450 | 12/1990 | Yokota | 348/72 |
| 5,018,509 | 5/1991 | Suzuki et al. | 348/71 |
| 5,090,400 | 2/1992 | Saito | 348/72 |
| 5,194,941 | 9/1993 | Grimaldi et al. | 348/596 |
| 5,196,928 | 3/1993 | Karasawa et al. | 348/65 |
| 5,209,220 | 5/1993 | Hiyama et al. | 348/72 |
| 5,213,092 | 5/1993 | Uram | 348/65 |
| 5,257,100 | 10/1993 | Hattori et al. | 348/72 |
| 5,291,010 | 3/1994 | Tsuji | 348/71 |
| 5,293,235 | 3/1994 | Guede et al. | 348/596 |
| 5,305,098 | 4/1994 | Matsunaka et al. | 348/72 |
| 5,309,227 | 5/1994 | Inoue | 348/587 |
| 5,347,987 | 9/1994 | Feldstein | 348/72 |

Primary Examiner—Tommy P. Chin
Assistant Examiner—A. Rao
Attorney, Agent, or Firm—Limbach & Limbach LLP

[57] ABSTRACT

A method for deriving an output signal from an input video signal generated by an image sensor having an image formed on a part of it. The input video signal includes an image portion generated by the part of the image sensor on which the image is formed, and an external portion generated by the part of the image sensor on which the image is not formed. In the method according to the invention, the input video signal is received, the external portion of the input video signal is identified, and the output signal is generated from the input signal by replacing the external portion with a synthesized portion. The synthesized portion may set the external area to black level, to a predetermined luminance and/or hue, or to a luminance and/or hue adaptively determined in response to the image portion of the input signal. A position-dependent variation may also be imposed on the external area. The external area may also be rearranged to change the displayed location of the image. The method also includes various ways of identifying the external portion of the input video signal.

15 Claims, 9 Drawing Sheets

VIDEO IMAGING SYSTEM WITH EXTERNAL AREA PROCESSING OPTIMIZED FOR SMALL-DIAMETER ENDOSCOPES

This is a continuation of application Ser. No. 08/074,110 filed on Jun. 9, 1993, now abandoned.

FIELD OF THE INVENTION

The invention relates to a method and apparatus for processing a video signal generated by an image sensor on which an image that occupies less than the total area of the sensor has been formed by a small-diameter endoscope.

BACKGROUND OF THE INVENTION

In fibre-optic endoscopes used in laparoscopy, a lens focuses an image of the object on the distal ends of a coherent bundle of optical imaging fibres. The image formed at the proximal end of the optical imaging fibres can be formed by a suitable lens into a real image for direct viewing, or can be focussed onto the image sensor of a video camera. The imaging bundle is surrounded by a layer of illuminating fibres through which light from a suitable high-intensity source is conducted to the distal end of the endoscope to illuminate the object.

Known video-based fibre-optic imaging systems are usually assembled from standard, commercially-available components: the image from the imaging bundle is focussed on the image sensor of a color video camera, and the resulting video signal is displayed on a commercial color video monitor. The illuminating fibres are normally illuminated with light generated by a 300-Watt Xenon-arc, a 150–300-Watt metal halide light source, or some other suitable light source. Video cameras used in known video-based imaging systems use systems developed for the consumer and industrial video markets to control parameters affecting image quality.

Most currently-available video-based fibre-optic imaging systems are optimized for large-diameter endoscopes having an outside diameter in the range of 5 to 10 mm (0.2" to 0.4") and using standard rod lens assemblies. Endoscopes having a considerably smaller outside diameter in the range of 1 to 2 mm (0.04" to 0.08") using Gradient Index (GRIN) lenses and fibre-optic imaging bundles have been developed and are also available for surgical applications. Such endoscopes are advantageous in that they further reduce the size of incision required to insert them into a body cavity.

While some known video imaging systems are capable of generating images from small diameter endoscopes, they are typically restricted to use at short working distances, typically less than 2" (50 mm). If the image from the fibre-optic assembly is formed on the image sensor in the camera so that the image covers the whole area of the sensor, the resulting video picture of an object at an extended working distance has insufficient intensity when normal levels of illumination are used. Moreover, the video picture of an object at any working distance is pixellated, i.e., the picture clearly shows the outlines of the individual optical fibres of the imaging bundle and the voids around them, if present. These shortcomings are a result of the small diameter of the imaging bundle, and the relatively few (typically 1,600 to 25,000) optical fibres in the imaging bundle of a small-diameter endoscope.

A more acceptable video picture is obtained by reducing the size of the image of the imaging bundle formed on the image sensor in the camera so that the image occupies a fraction of the area of the sensor. This arrangement produces a video frame in which a central image of the imaging bundle is surrounded by a blank external area, and results in a video picture in which the intensity of the image is increased and the pixellation of the image is reduced. However, this arrangement also has some disadvantages. The pixels of the image sensor in the external area surrounding the image generate noise, especially when the light level of the image is low. This noise is visible in the blank external area of the frame, and can be distracting to the observer.

Small-diameter fibre-optic endoscopes present additional problems when used in large body cavities. In such applications, endoscopes with a hyper-extended working distance, greater than 50 mm (2"), are used. With such an arrangement, the light level on the sensor in the video camera is low, which exacerbates the noise problem in the external area surrounding the image.

In known video display systems for small-diameter endoscopes, the location of the image in the frame displayed on the monitor corresponds to the location of the image on the image sensor in the camera. Thus, the image is nominally displayed in the center of the monitor screen, but the position of the image on the sensor, and hence on the screen, is not accurately determined due to mechanical tolerances in the optical assembly. This layout requires the use of external equipment, such as a video switcher, to be able to display auxiliary information, such as patient monitoring data, or video system parameters, in the external area outside the image, or to be able to display multiple endoscope images on the same monitor. However, satisfactory results are not always obtained because of tolerance in the position of the image on the sensor.

Additionally, displaying the image in the same place on the monitor screen can, over time, cause a sharply-delineated burn area on the screen. The boundary of the burn area becomes noticeable if the diameter of the image increases, or if the position of the image on the screen changes. Screen burn is exacerbated if the image is always displayed in the same position on the screen.

It is known in consumer video systems to derive a signal for operating an auto focus system from an small area, normally in the center, of the image sensor in the camera. It is also known in endoscopic video systems to derive a signal for adjusting white balance from a small area, normally in the center, of the image sensor in the camera. In both of these known systems, however, the relationship between the small area and the image is undefined.

OBJECTS AND SUMMARY OF THE INVENTION

It is an object of the present invention to provide a video-based fibre-optic imaging system in which the image of the imaging bundle of a small-diameter endoscope is formed on less than the total area of the image sensor, and in which the small-diameter endoscope is automatically detected, and the video processing required as a result of the image being formed on less than the total area of the image sensor is automatically selected in response to such detection.

It is an object of the present invention to provide a video-based fibre-optic imaging system in which an image of the imaging bundle is formed on less than the total area of the image sensor, and in which parameters relating to the video picture are detected according to the type of endoscope connected to the system.

It is an object of the present invention to provide a video-based fibre-optic imaging system in which an image of the imaging bundle is formed on less than the total area of the image sensor, and in which degradation of picture quality by noise in the external area of the video picture surrounding the image is avoided.

It is an object of the present invention to provide a video-based fibre-optic imaging system in which an image of the imaging bundle is formed on less than the total area of the image sensor, and in which the external area of the video picture surrounding the image can be set to a predetermined luminance and hue.

It is an object of the present invention to provide a video-based fibre-optic imaging system in which an image of the imaging bundle is formed on less than the total area of the image sensor in the center of the image sensor, and in which the image can be displayed at a repeatable location in any position on the monitor.

Accordingly, the invention provides a method of deriving an output video signal from an input video signal generated by an image sensor having an image formed on a part of it. The input video signal includes an image portion generated by the part of the image sensor on which the image is formed, and an external portion generated by the part of the image sensor on which the image is not formed. In the method according to the invention, the input video signal is received, the external portion of the input video signal is identified, and the output signal is generated from the input signal by replacing the external portion with a synthesized portion.

The synthesized portion replaces the noisy external portion of the input signal with a black level, a predetermined luminance and hue, an adaptively-determined luminance and hue, or data in the external area.

When the image is formed on part of the image sensor by one of plural types of image-forming apparatus, the type of image-forming apparatus forming the image is determined, and the external portion of the input video signal is identified in response to the determination of the type of image-forming apparatus.

When only one type of image-forming apparatus forms the image on part of the image sensor, it is determined when the one type of image-forming apparatus is forming the image on pan of the image sensor, and the external portion of the input video signal image is identified in response to the determination that the one type of image-forming apparatus is forming the image on part of the image sensor.

When the image is formed on part of the image sensor by an image-forming apparatus that has stored in it image information for the image-forming apparatus, the stored image information for the image-forming apparatus is retrieved from the image forming apparatus, and the image portion of the input video signal is identified using the retrieved stored image information. Image information is information identifying the image portion of the input video signal generated by the part of the image sensor on which the image is formed by the image-forming apparatus.

The image portion of the input video signal may alternatively or additionally be identified by determining the lines of the input video signal that include an image part generated by the part of the image sensor on which the image is formed, and an external part generated by the part of the image sensor on which the image is not formed. Then, for each line so identified, the position of the boundary between the image part and the external part is determined.

When the image formed on part of the sensor has a known shape, but an unknown position on the image sensor, and an unknown size, the image portion of the input video signal may be identified by analyzing the input video signal to determine parameters for calculating the size and the position of the image on the image sensor. Then, the boundary lines having an image portion and an external portion are calculated from the determined parameters and the known shape of the image. Finally, for each boundary line, the position of the boundary between the image part and the external part is calculated.

The method may additionally comprise the step of selectively delaying one of the image portion and parts of the synthesized portion of the input video signal with respect to the other before including the image portion and the synthesized portion in the output video signal, such that, when the output video signal is displayed, the image portion in the output video signal is displayed in a position different from a position corresponding to the position of the image on the image sensor.

The invention also provides an apparatus for deriving an output video signal from an input video signal generated by an image sensor having an image formed on a part of it. The input video signal includes an image portion generated by the part of the image sensor on which the image is formed, and an external portion generated by the part of the image sensor on which the image is not formed. The apparatus comprises a frame store memory for storing either the input signal or the output signal and a digital signal processor, operating in cooperation with the frame store memory. The digital signal processor is programmed to identify the external portion of the input video signal, and to generate the output signal from the input signal by replacing the external portion with a synthesized portion.

BRIEF DESCRIPTION OF THE DRAWINGS

FIG. 9A shows the location on the image sensor of certain pixels in the image;

FIG. 9B shows the location in the frame store of the samples corresponding to the pixels in the image; and FIG. 9C shows the location on the display screen of the pixels corresponding to the samples in the frame store.

DETAILED DESCRIPTION OF THE INVENTION

Figure 1:
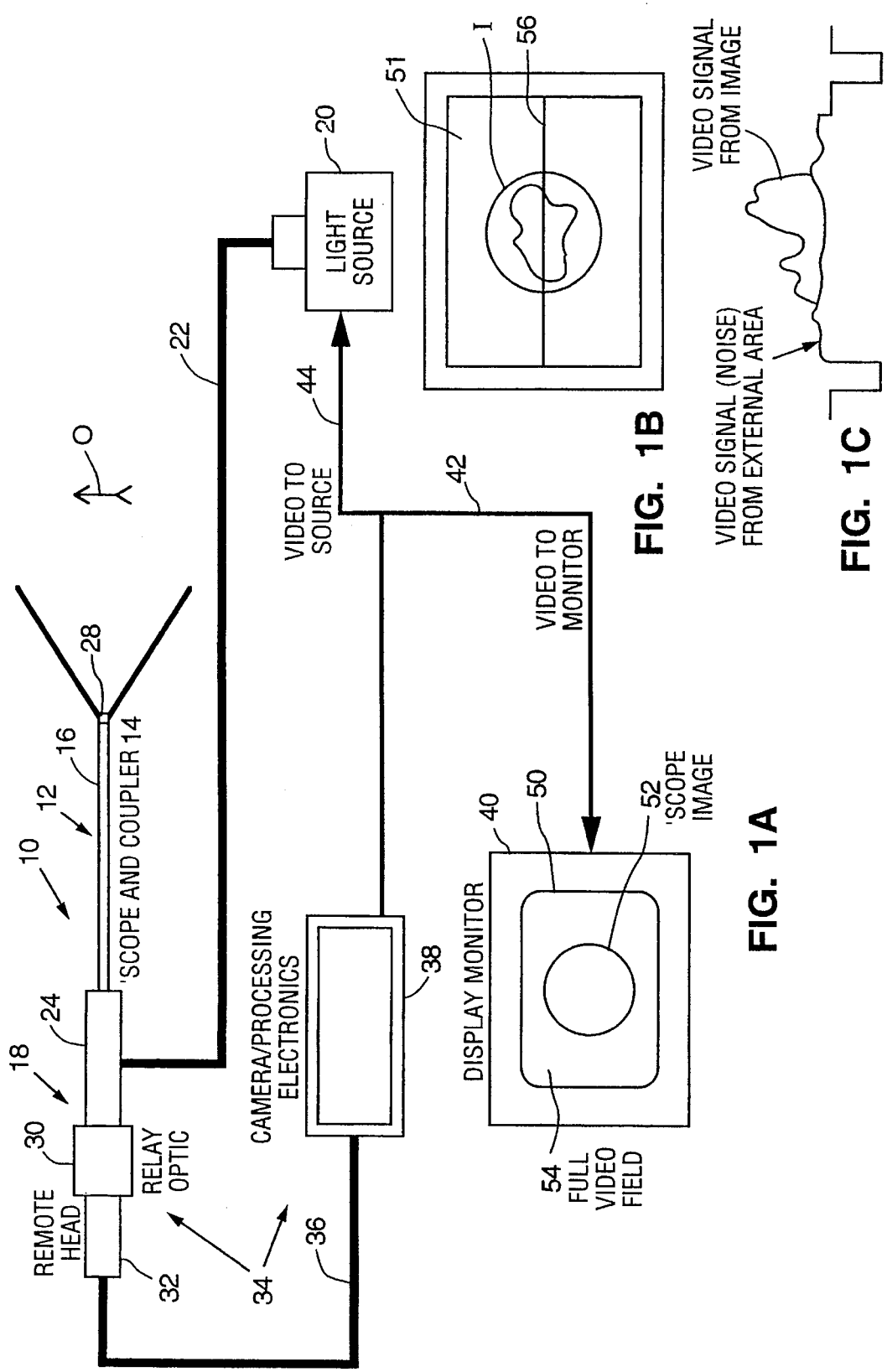
FIG. 1A shows a block diagram of a known video-based fibre-optic imaging system.
FIG. 1B shows an image of the proximal end of the imaging bundle formed on a part of the area of the image sensor in a known video-based fibre-optic imaging system.
FIG. 1C shows one line of the video signal generated from the image sensor shown in FIG. 1B.

FIG. 1A shows a block diagram of a known video-based fibre-optic imaging system for use with an endoscope, or other optical instruments. In FIG. 1A, the endoscope 10 includes the fibre-optic assembly 12, a coaxial or parallel arrangement of the inner imaging fibre-optic bundle 14 and the outer illuminating fibres 16. The imaging bundle normally includes between 1,600 and 25,000 optical fibres.

The fibre-optic assembly 12 is detachably attached to the optical assembly 18. This allows a common optical assembly 18 to be used with fibre-optic assemblies optimized for different working distances, and also allows disposable fibre-optic assemblies to be used.

The optical assembly 18 couples light transmitted from the light source 20 through the fibre-optic bundle 22 and the coupler 24 into the illuminating fibres 16. Light emitted from the distal end of the illuminating fibres illuminates the object O. Light from the object O is gathered by the lens 28 on the distal tip of the imaging bundle 14, and transmitted through the imaging bundle into the optical assembly 18. The object O may well be situated at an extended working distance from the distal tip of the endoscope 10. However, the invention is equally applicable to endoscopes used at non-extended working distances.

The optical assembly 18 also includes the relay optic 30, which forms a real image of the proximal ends of the optical fibres of the imaging bundle 16, including the transmitted image of the object O, on the remote head 32 of the video camera 34. The remote head 32 includes an image sensor, which is a preferably charge-coupled device (CCD) array with color filters formed on the sensor surface. The remote head also includes the drive circuitry and video amplifier for the CCD array. A 784×492-element CCD array with 385,728 pixels is used in the preferred embodiment, and will be referred to in the various examples to be described below. CCD arrays with alternative pixel arrangements can equally be well used. Plural CCD arrays with color filters, or a CCD array without color filters can also be used.

The cable 36 connects synchronizing pulses from the camera electronics 38 to the remote head 32, and connects the video output of the remote head to the camera electronics. This video output could be an analog video signal, with or without synchronizing pulses, or could be a digital bit stream representing a video signal, or could be pixel data. The camera electronics derive a normal NTSC composite video signal or a component video signal frown the video output from the remote head.

The camera electronics normally include circuitry for automatically adjusting the white balance of the video signal, and normally also include an automatic shutter circuit and an automatic gain control. The automatic shutter circuit varies the integration time of the CCD array to keep the luminance level of the video signal generated by the remote head within a predetermined range.

The video signal 42 from the camera electronics 38 is fed to the video monitor 40. The camera electronics may also feed the video signal via the path 44 to the light source 20 to provide a feedback signal thereto, in which case, the automatic shutter and gain controls in the camera are preferably defeated. The feedback signal is used by a servo that controls a motorized shutter varying the light output of the light source 20 to keep the luminance level of the video signal within a predetermined range. However, most systems currently in use rely on an electronic shutter circuit in the camera to maintain the luminance level of the video signal 42.

When the fibre-optic assembly 12 has a small diameter, e.g., an outside diameter of less than 2 mm, the optical assembly 18 forms an image I of the proximal end of the imaging bundle 14 on only part of the area of the CCD array 51 in the remote head 32, as shown in FIG. 1B. This is done to provide an adequate light level on the part of the CCD array on which the image is formed, and hence image brightness, and to avoid obvious pixellation, as described above. One typical line of the resulting video signal is shown in FIG. 1C.

The resulting video picture is shown on the monitor 40 in FIG. 1A. Only part of the frame 50 is occupied by the image 52 of the proximal end of the imaging bundle 14. The external area of the video frame surrounding the image is nominally blank, but includes noise generated by the unilluminated pixels of the CCD array, as shown in FIG. 1C. The noise is especially severe when the light level falling on the pixels of the CCD array on which the image is formed is low, and the automatic shutter control in the camera increases the integration time to provide the predetermined video signal level. Noise reduces the apparent quality and contrast of the image, and is distracting to the observer.

Figure 2:
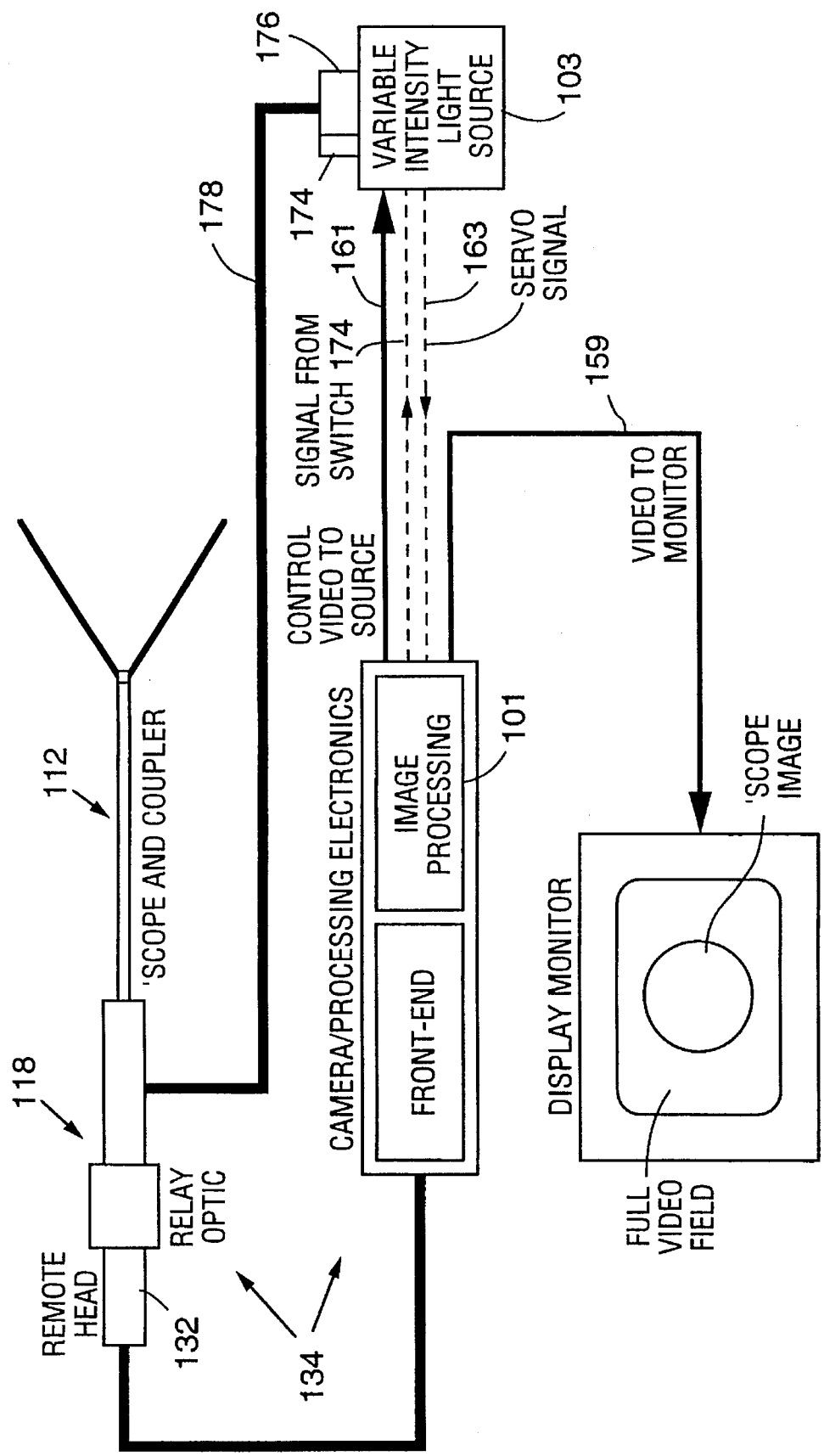
FIG. 2 shows a block diagram of a video-based fibre-optic imaging system according to the invention.

FIG. 2 is a block diagram of a video-based fibre-optic imaging system according to the invention for use with an endoscope, or other optical instrument. The imaging system according to the invention can be used with endoscopes of all diameters, but is most advantageous when used with a small-diameter endoscope that forms an image on less than the full area of the image sensor in the camera. Components in the imaging system according to the invention that are the same as components of the known imaging system are indicated with the same reference number.

In the imaging system shown in FIG. 2, the video output from the remote camera head 132 is processed by the image processing electronics 101. The image processing electronics automatically determine when the image is formed on less than the full area of the CCD array. In response to this determination, the image processing electronics process the part of the video signal generated in response to the external area to eliminate noise in the external area. The image processing electronics also allow the user to place the image in any desired location in the video frame. This makes it more convenient to display other information together with the image in the video frame.

The video imaging system shown in FIG. 2 preferably also includes the variable-intensity light source 103 controlled by a signal derived from the image only. The signal-to-noise ratio of the video images produced by the imaging system according to the invention is improved compared with a conventional fibre-optic imaging system because, compared with the conventional system, the video imaging system according to the invention operates with a higher maximum illumination level from the light fibres and a higher maximum illumination level returning to the fibre-optic imaging components. Alternatively or additionally, the imaging system according to the invention may provide a signal derived from the image only to control the automatic shutter system in the camera to provide a more accurate exposure adjustment.

Figure 3:
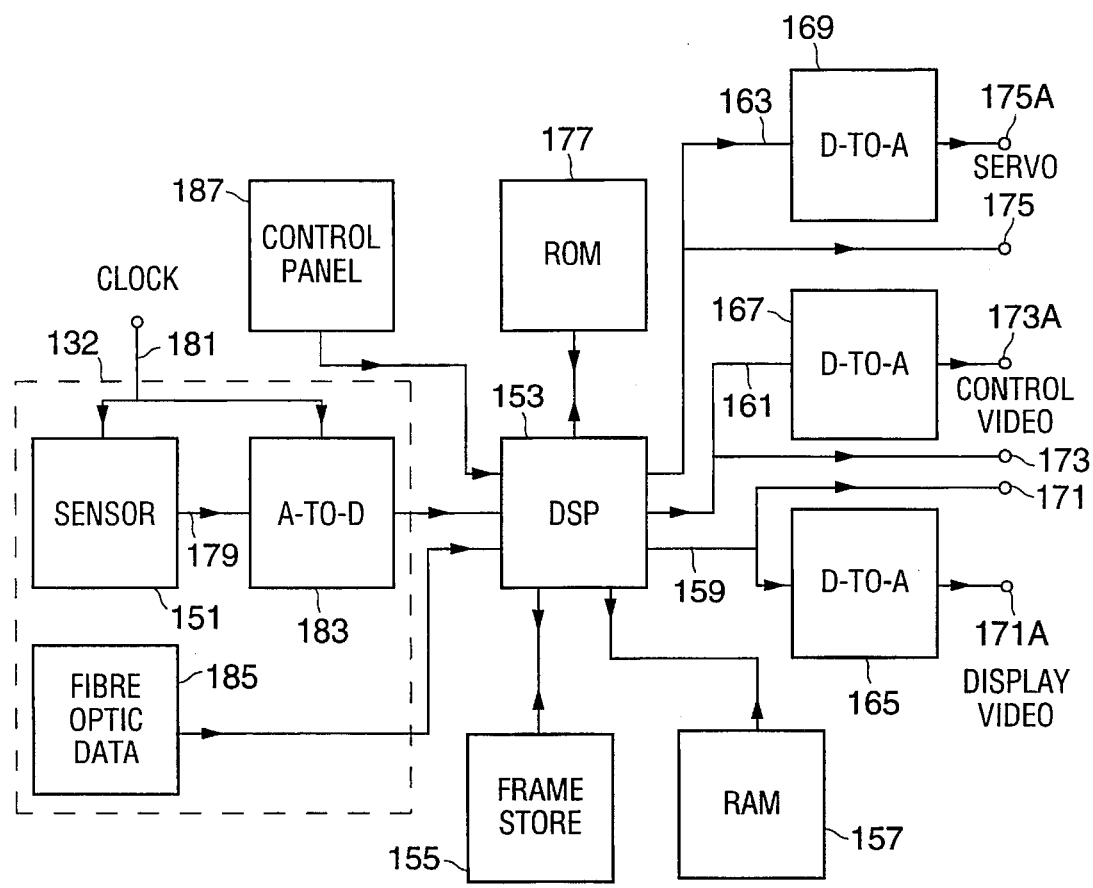
FIG. 3 shows a block diagram of the image processing electronics of a video-based fibre-optic imaging system according to the invention.

A block diagram of the preferred embodiment of the image processing electronics 103 is shown in FIG. 3. The preferred embodiment digitizes the output of the CCD array 151, and uses the video digital signal processor (DSP) 153 and its associated memories 155 and 157 to carry out the image processing to be described below.

The digital signal processor also encodes the image-processed digital video signal into a digital display video output 159. In the following description, an embodiment producing an NTSC composite video signal as the digital display video output will be described, but the principles described herein can readily be adapted to produce other format composite video signals., e.g., PAL, SECAM, component video signals, e.g., S-video, Y,I,Q, or high-definition video signals.

The digital video display signal 159 is fed to the output terminal 171 for connection to the parts of rest of the system that require a digital signal, and is also fed to the digital-to-analog converter 165 where it is converted into an analog signal, which is fed to the output terminal 171A for connection to the parts of the rest of the system requiring an analog signal.

Alternatively, the image processing electronics can be provided using different arrangements of digital circuitry, or by analog processing.

The digital signal processor 153 executes a main routine that can call various routines to perform the different aspects of image processing. The routines are stored in the Read-only Memory 177 or in some other form of non-volatile memory. Working results and other data are stored in the Random Access Memory (RAM) 157.

The video output 179 of the CCD array 151, produced in response to the clock signal 181, is fed into the analog-to-digital converter 183, which converts the analog voltage generated by each pixel of the array into a sample, which is preferably an 8-bit binary number. The resulting samples are fed into the DSP 153, which stores the set of samples for one frame generated by one scan of the CCD array in the frame store memory 155. The samples are preferably stored in a matrix arrangement of memory elements corresponding to the lines and pixels of the CCD array so that the memory location in which the sample for an individual pixel is stored can be addressed using the line number and pixel number of the pixel.

The DSP 153 derives each frame of the digital video output signal 159 and the digital control video signal 161 by sequentially reading each pixel of the frame from the frame store 155, and applying appropriate processing.

Each of the various processing operations of the DSP 153 will now be described.

IMAGE BOUNDARY DETECTION

In this processing operation, the digital signal processor determines, in terms of lines and pixels, an image boundary table defining the area of the CCD array on which the image is formed. The image boundary table, which is stored in the RAM 157, is then used to process the data received from the image sensor 151.

In the following explanation, a pixel on which the edge of the image falls will be called a "boundary pixel." Each line that includes a boundary pixel will be called a "boundary line." Since the image is substantially symmetrical, each boundary line includes two boundary pixels, a left boundary pixel and a right boundary pixel. The boundary lines closest to the top of frame and to the bottom of the frame will be called the "top boundary line" and the "bottom boundary line," respectively.

Two main types of image boundary detection will be described. In the first main type, the DSP 153 simply retrieves stored image boundary parameters defining a boundary table or from which a boundary table can be calculated. In the second main type, the DSP executes a routine that determines the image boundary empirically. Image boundary parameters can be used as the sole means tier determining the image boundary if close tolerances can be guaranteed in the optical system. If close tolerances cannot be guaranteed, and the size and position of the image on the image sensor can vary, a combination of image boundary parameters and empirical determination is preferably used to determine the image boundary. The image boundary parameters simplify and speed up the empirical determination algorithm.

In the first main type of boundary detection, the image boundary parameters may be stored in the image processing electronics 101, or in the fibre-optic assembly 112. Plural sets of parameters may be stored in the image processing electronics 101, and the appropriate set of parameters for the fibre-optic assembly being used may be automatically selected.

The image boundary parameters could be the actual values of the image boundary table, or could include information indicating the pixel numbers of the left and right boundary pixels (if any) for each line of the video frame, or information from which these pixel numbers can be determined. The information from which the pixel numbers of the boundary pixels on each line can be determined could be in the form of a table defining whether or not the image is formed on each pixel on each line of the frame, or a table defining the pixel number of the boundary pixels of each line. Alternatively, image boundary parameters, such as those defining the shape of the image, the location of its center, and its size, could be inserted into an algorithm that calculates the boundary table.

The image boundary table could consist of a flag bit for each pixel of the CCD array 151. In response to the parameters retrieved from storage, the DSP 153 sets each flag bit in the flag section according to whether the image is formed on the pixel corresponding to the flag bit. Alternatively, the image boundary table could consist of a number pair for each line. The number pair consists of the two pixel numbers of the boundary pixels of each line. The number pair for each line which is not a boundary line would include a number outside the range of pixel numbers, e.g., a number greater than 783, to indicate that the line is not a boundary line.

Preferably, the image boundary table stores a number pair for each boundary line, plus an additional number pair. The additional number pair consists of the line numbers of the top and bottom boundary lines. The rest of the number pairs consist of a number pair for each boundary line between the top boundary line and the bottom boundary line, inclusive. The number pair consists of the pixel numbers of the left and right boundary pixels. The image boundary table stored in the RAM 157 is used by the DSP 153 in performing the image processing that will be described below.

Stored Image Boundary Parameters

In this approach, a switching arrangement detects connection of a small-diameter fibre-optic assembly to the optical assembly. When a small-diameter fibre-optic assembly is detected, the digital signal processor retrieves the image boundary parameters from a memory.

Small-Diameter Fibre-Optic Assembly Detection

Figure 4A:
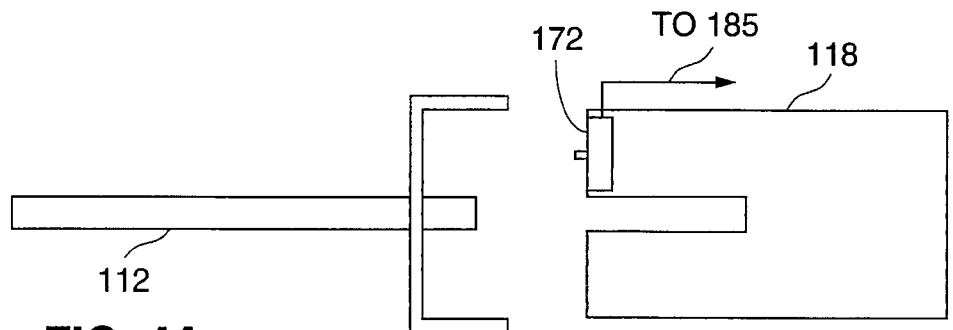
FIG. 4A shows an endoscope incorporating automatic switching for a small-diameter fibre-optic assembly according to the invention.

FIG. 4A shows the switch 172 built into the optical assembly 118. The switch 172 may be a mechanical or an LED switch, or some other suitable type of switch. The switch is activated when a small-diameter endoscope is attached to the optical assembly, but not when a normal-diameter fibre-optic assembly is attached to the optical assembly.

Alternatively, a shown in FIG. 2, the switch 174 may be built into the connector 176 in the variable intensity light source 103. Such light sources have plural connectors for different types of illuminating fibre cables. The connector 176 is for the illuminating fibre cable 178 of a small-diameter fibre-optic assembly. Thus, the switch 174 would be activated when the illuminating fibre cable 178 of a small-diameter fibre-optic assembly is plugged into the connector 176, but would not be activated when the illuminating cable assembly of a large-diameter fibre-optic assembly were plugged into a different connector on the light source 103.

The signal from the switch 172 or 174 is received by the fibre-optic data unit 185, which passes the signal to the DSP 153. In response to the signal, the DSP retrieves a set of image boundary parameters from a memory, such as the RAM 157 or the ROM 177, and begins processing data received from the sensor 151 in response to the image boundary data. This arrangement works with an endoscope that can accept only a single type of small-diameter fibre-optic assembly. The image boundary data pertaining to this single type of fibre-optic assembly would be stored in the memory. Even if a different type of small-diameter fibre-optical assembly were used with his arrangement, the results, although inaccurate, may better than having no image processing at all.

Fibre-Optic Assembly Type Sensing

This arrangement provides accurate processing of the image with plural types of fibre-optic assembly. In this arrangement, shown in FIG. 4B, each type of fibre-optic assembly would be coded with a type identification number that identifies the type of the fibre-optic assembly. When the fibre-optic assembly is attached to the optical assembly, the type identification number would read out, and the DSP 153 would retrieve from a memory the image boundary data pertaining to the type of fibre-optic assembly identified by the time identification number. The DSP would then process the data from the sensor 151 according to the image boundary data. The type identification number could be stored using a simple arrangement, for example, holes in the fibre-optic assembly could operate mechanical or LED switches built into the optical assembly 118; or some other arrangement could be used.

Figure 4B:
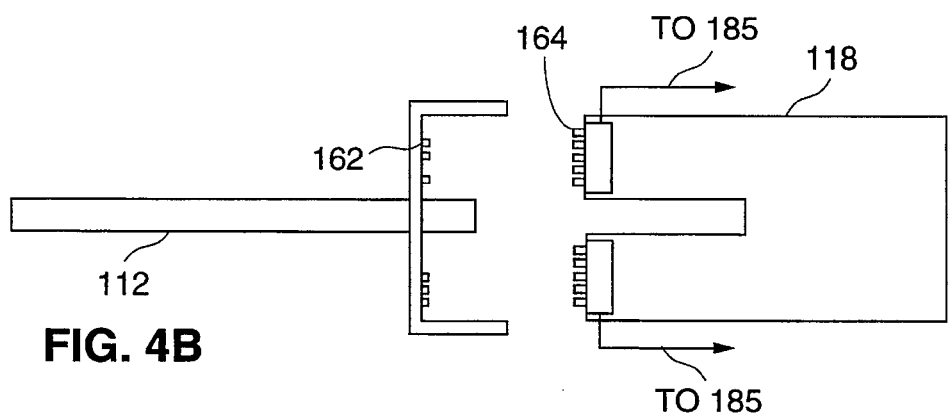
FIG. 4B shows an endoscope incorporating automatic type identification according to the invention.

FIG. 4B shows the fibre-optic assembly 112 having a coded arrangement of cams 162. The cams operate contacts in a bank of micro switches 164 built into the optical assembly 118. When the fibre-optic assembly is attached to the optical assembly, the cams change the state of certain ones of the micro switches. The outputs of the micro switches are fed into the fibre-optic data unit 185 as the type identification number of the fibre-optic assembly. Alternatively, the type identification number could be stored in a read-only memory built into the fibre-optic assembly. In an arrangement similar to that which will be described below, the fibre-optic data unit 185 would retrieve the type identification number from the read-only memory.

The fibre-optic data unit 185 transmits the type identification number of the fibre-optic assembly to the DSP 153, which looks up the image boundary parameters, and such other parameters as the working distance, shape, size, orientation, f-number, number of fibres, radial non-linearity, etc., for the fibre-optic assembly in response to the type identification number. These parameters for a number of different types of fibre-optic assembly would be stored in a look-up table in the RAM 157, the read-only memory 177, or in some other memory.

Data Retrieval from the Fibre-Optic Assembly

Figure 4C:
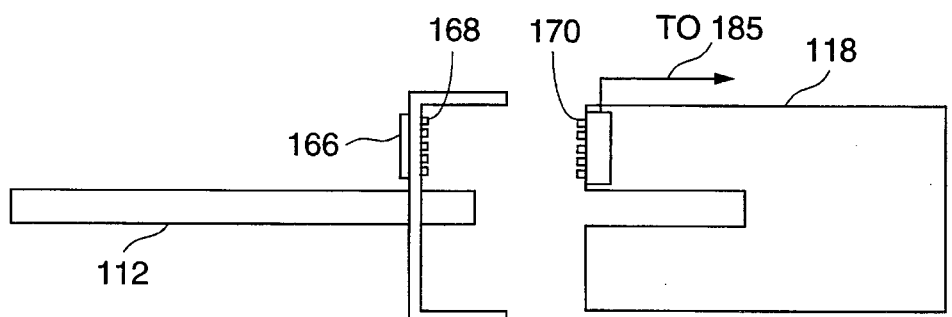
FIG. 4C shows an endoscope incorporating a memory from which image processing parameters can be retrieved according to the invention.

Instead of being coded with a type identification number, each fibre optic assembly could store data defining the image boundary parameters, and such other parameters as the working distance, size, shape, f-number, orientation, number of fibres, radial non-linearity, etc. for the fibre-optic assembly. FIG. 4C shows an arrangement in which the parameters are stored in the read-only memory 166 built into the fibre-optic assembly. Opposing contacts 168 and 170 on the fibre-optic assembly 112 and the optical assembly 118 allow the DSP 153 to interrogate this memory via the fibre-optic data unit 185.

Any change in the data fed to the DSP 153 by the fibre-optic data unit 185 would cause the DSP execute a set-up routine. The image boundary parameters retrieved from the read-only memory 166 will indicate whether the image fills the sensor. If the image boundary parameters indicate that the image is formed on only a pan of the sensor, image processing is required, and the DSP 153 will store the image boundary parameters and the other parameters in the RAM 157, and carry out image processing in response to them.

Universal Image Boundary Detection

In this approach, the location of the boundary pixels on each line on which the image falls is determined by examining the digital video samples stored in the frame store 155. This approach allows any kind of fibre-optic assembly to be use since it does not require a special fibre-optic assembly in which data is stored. This approach also enables variations and errors in the optical assembly 118 to be taken into account. The DSP 153 can execute the set-up routine shown in FIG. 5 when the system is switched on, or in response to the fibre-optic data unit 185 detecting that a fibre-optic assembly has been connected to the optical assembly 118. This requires a switch operated by connecting the fibre-optic assembly to the optical assembly, similar that shown in FIG. 4A. Alternatively, the DSP 153 can detect black level (or a low level) at several points near the perimeter of the sensor, indicating that the image is formed on less than the full area of the image sensor, and execute the set-up routine in response to this detection. During execution of the set-up routine, the optical assembly is pointed at a well-illuminated target.

It is preferred that the set-up routine be executed after the optical assembly has been focussed. Execution of the set-up routine can be triggered by the user operating an appropriate control on the control panel 187 after the optical assembly has been focussed. Alternatively, the set-up routine can be adapted to perform a rough determination of the location of the boundary pixels, and to monitor the sharpness of the boundary. Only after the set-up routine determines that the boundary has the degree of sharpness resulting from the optical assembly being properly focussed will the set-up routine perform a final, accurate determination of the location of the boundary pixels.

Since, with some optical systems, the image size changes when the focus is changed, the DSP 153 can be programmed to execute a check routine that checks whether the image boundary coincides with the image boundary determined by the set-up routine. For simplicity, the check routine can check a number of sample points on the image boundary instead of every point on the image boundary. The check routine could be executed in response to a determination that an auto-focus circuit has changed the focus. Alternatively, the check routine could be used to provide focussing data to control an auto-focus system.

If the check routine determines that the image boundary does not coincide with the image boundary determined by the set-up routine, the check routine causes the set-up routine to re-execute. The check routine also checks the illumination level at several points near the image boundary, and only instigates re-execution of the set-up routine when a boundary discrepancy is detected, and the illumination levels are determined to be high enough to ensure that the set-up routine will produce a reliable result. Alternatively, or additionally, the check routine could display a message on the monitor 40 indicating that the set-up routine was executing and prompting the user to direct the fibre-optic assembly towards a bright object.

Figure 5:
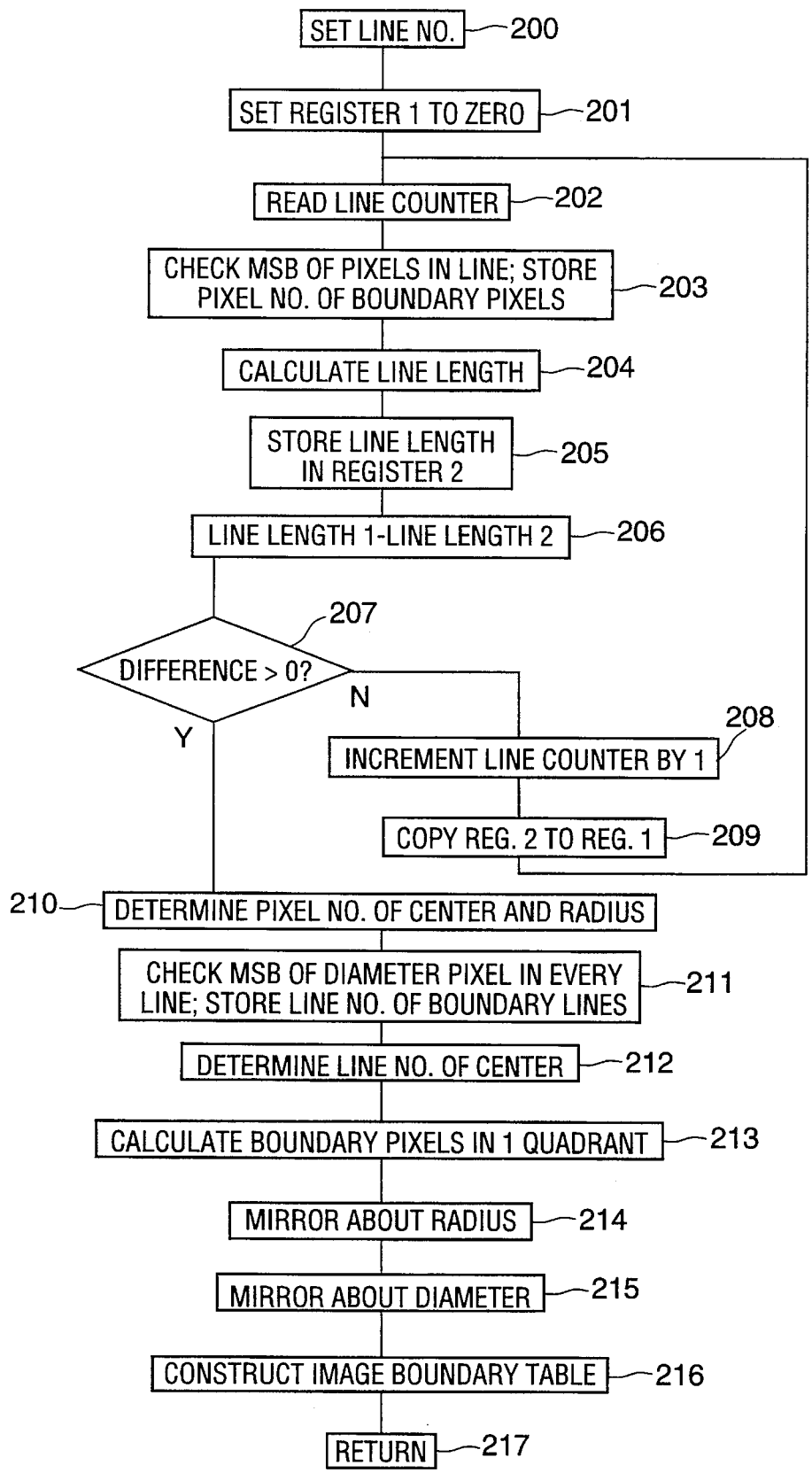
FIG. 5 shows a flow chart of the set-up routine in a video-based fibre-optic imaging system according to the invention.

The set-up routine shown in FIG. 5 assumes that a circular image is roughly centered on the CCD array. The routine could also be adapted to operate an image that has a known, but non-circular, shape. The routine first determines the radius of the image and the line number and pixel number corresponding to the center of the image. From this data, the routine generates values for an image boundary table by calculating the pixel numbers of the two boundary pixels on each line on which the image falls.

Figure 6A:
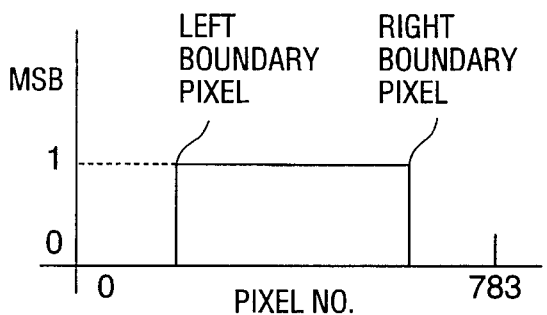
FIG. 6A is a graph showing the state of the most significant bit of the sample derived from each pixel along one line on which the image falls.

The state of the most significant bit (MSB), or of some other high-order bit, of the samples corresponding to the pixels on each line on which the image falls has the form shown in FIG. 6A. The MSB changes state at the two points on the line corresponding to the boundary of the image falling on the line. The pixel number of the boundary pixel, at which the MSB changes state, changes from line-to-line.

In step 200, the DSP 153 sets the value stored in a line counter to a predetermined value corresponding to the line number of a line above the center of the CCD array. In step 201, the DSP sets the line length stored in a first register to zero. In step 202, the DSP reads the value stored in the line counter.

In step 203, the DSP 153 examines the state of the MSB of the sample for each pixel in the line having a line number defined by the line counter, and stores the pixel numbers of the two boundary pixels at which the MSB changes state in a second register.

At step 204, the DSP 153 calculates the difference between the two pixel numbers determined in step 203. This difference will be called the line length. The line length of a line indicates the number of pixels in the line on which the image falls. At step 205, the DSP stores the line length, also in the second register.

At step 206, the digital signal processor subtracts the line length stored in the second register from the line length stored in the first register. At step 207, the DSP tests whether the result of the subtraction is greater than or equal to zero. In this first iteration of the routine, the test result is NO, because of the initial value of zero stored in the first register. Accordingly, the routine proceeds to step 208, where the line counter is incremented by 1, and to step 209, where all the values in the second register are copied into the first register, after which execution returns to step 202.

In the second and subsequent iterations, at step 202, the DSP 153 reads the value in the line counter, and at step 203, the DSP examines the state of the MSB of the sample of each pixel in the "current" line which is the line having a line indicated by the value in the line counter. The current line is the line below the "previous" line, which is the line examined in the previous iteration. The DSP determines the pixel numbers of the two boundary in the current line at which the MSB changes state. At step 204, the digital signal processor calculates the line length of the current line by taking the difference between the two pixel numbers, and at step 205 stores the line length of the current line in the second register.

At step 206, the digital signal processor subtracts the line length stored in the second register (i.e., the line length of the current line) from the line length stored in the first register (i.e., the line length of the previous line). When, at step 207, the DSP tests whether the resulting difference is greater than or equal to zero, the result will be NO if the line length of the current line is greater than the line length of the previous line. This occurs when the previous line and the current line are both above the line corresponding to the diameter of the image. In this case, execution proceeds to steps 208 and 209, and then reverts to step 202.

If the subtraction at step 206 produces a positive or zero result, and the result of the test at step 207 is YES, this indicates that the line length of the current line is less than or equal to the line length of the previous line. This occurs when the current line and the previous line bridge the diameter of the image (zero result) or when the current line is one line below the diameter, and the previous line is the diameter. In this case, execution passes to step 210, where one is subtracted from the value of the line counter, and the result is stored as the line number of the center of the image. The pixel number of the center of the image is determined by subtracting the left boundary pixel number stored in the first register from the right boundary pixel number stored in the first register, i.e., the boundary pixel numbers of the previous line. The difference is divided by two to provide the radius of the image. The radius is then added to the left boundary pixel number to determine the pixel number of the center of the image.

The part of the algorithm just described accurately determines the radius of the image, and the pixel number of the center of the image, but, because the line length changes relatively slowly in the vicinity of the diameter, the line number of the center of the image is less accurately determined. The next part of the algorithm accurately determines the line number of the center of the image.

Figure 6B:
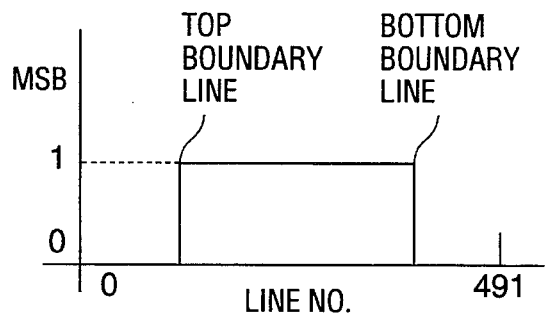
FIG. 6B is a graph showing the state of the most significant bit of the sample derived from the pixel having a pixel number equal to the pixel number of the center of the image on each line of the frame.

In step 211, the DSP 153 examines the state of the MSB of the sample in each line corresponding to the pixel having the same pixel number as that the center of the image determined in step 210. The state of the MSB of the pixels having the same pixel number in each line has the form shown in FIG. 6B. The DSP stores the line numbers of the top and bottom boundary lines, at which the MSB changes state.

At step 212, the DSP 153 determines the line number of the center of the image by subtracting the top line number from the bottom line number, dividing the resulting difference by two, and adding the resulting quotient to the top line number. This step may also provides the radius of the image, and may compare this radius it with the radius calculated in step 210. If the two results do not agree, steps 202 through 210 can be repeated. Alternatively, the accuracy of the image boundary calculation performed in the following steps can be increased by regarding the image as an ellipse, and using the radii calculated in steps 210 and 212 as the axes of the ellipse.

In step 213, the pixel number of one boundary pixel, e.g., the left boundary pixel, on each line corresponding to a quadrant of a circle or ellipse are calculated for each line from the center and radius calculated in steps 210 and 212. In step 214, the pixel number of the other boundary pixel, e.g., the right boundary pixel, in each line for one half of the image is calculated by mirroring the pixel numbers calculated in step 213 about the radius of the image. Finally, in step 215, the pixel numbers of both boundary pixels in each line in the rest of the image are calculated by mirroring the pixel numbers calculated in steps 213 and 214 about the diameter of the image.

As an alternative to the line-by-line and pixel-by-pixel approach just described, a routine similar to that just described could be used to find the pixel numbers of the boundary pixels on several lines in the image sensor. Then, a curve fitting routine could be used to determine the pixel numbers of the boundary pixels on all lines in the image, and the line number and pixel number of the pixel corresponding to the center of the image.

The results of the above calculations are placed in the image boundary table stored in the RAM 157. As described above, the image boundary table preferably consists of a number pair for each boundary line, plus an additional number pair. The additional number pair consists of the line numbers of the top and bottom boundary lines. These line numbers are determined in step 212. The rest of the number pairs consist of a number pair for each boundary line between the top boundary line and the bottom boundary line, inclusive. Each number pair consists of the pixel numbers of the left and right boundary pixels of the line. Alternatively, a number pair can be stored for each line, irrespective of whether the line is a boundary line. The number pair for each line which is not a boundary line would include a number outside the range of pixel numbers, e.g., greater than 784, to indicate that the line is not a boundary line.

Once the set-up routine has been completed, the digital signal processor returns to its main routine.

EXTERNAL AREA PROCESSING

Basic Image/External Area Processing Routine

In this process, the digital signal processor (DSP) 153 eliminates noise in the external area of the picture by storing the sample values of only those pixels on which the image falls in the corresponding memory locations in the frame store 155. For the pixels in the external area of the frame, surrounding the image, the DSP stores a predetermined value in the corresponding memory locations in the frame store 155. Alternatively, the size of the frame store 155 may be reduced to that required to store the sample values for the largest image formed on the image sensor. In this case, the frame store does not store values corresponding to the predetermined value in the external area, and the DSP generates or synthesizes a value corresponding to the predetermined value "on the fly," when needed for the external area.

In a first embodiment, the digital signal processor sets the predetermined value for each pixel in the external area to a value corresponding to black level, or near black level. In a first alternative embodiment, the digital signal processor sets the predetermined value for each pixel in the external area to a value corresponding to a predetermined luminance level and a predetermined hue. In a second alternative embodiment, the digital signal processor adaptively sets the predetermined value for each pixel in the external area to a luminance level and a hue determined in response to the luminance level and hue of the image area to enhance the viewer's perception of the image. In a variation on either of the alternative embodiments, a radial variation, or some other position-dependent variation, may be imposed on the luminance level and hue of the pixels in the external area. The variation may be predetermined or may be adaptively determined by the luminance level and hue of the image.

In the above processing, the external area need not be processed every frame: once DSP has set the memory locations corresponding to the external area to black level or to a level corresponding to a predetermined luminance and/or hue, the values in the memory locations corresponding to the external area need only be changed if the image boundary changes. Even when the memory locations corresponding to the external area are set to an adaptively-determined level, this processing need not be carried out every frame.

Figure 7D:
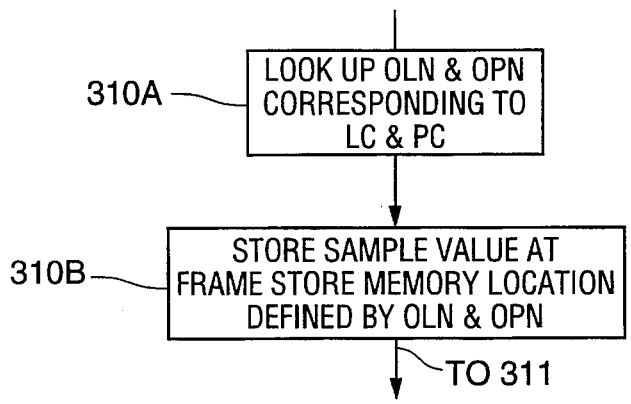
FIG. 7D is a flow chart showing how step 310 of the routine shown in FIG. 7A is modified to relocate the image on the screen.
Figure 7A:
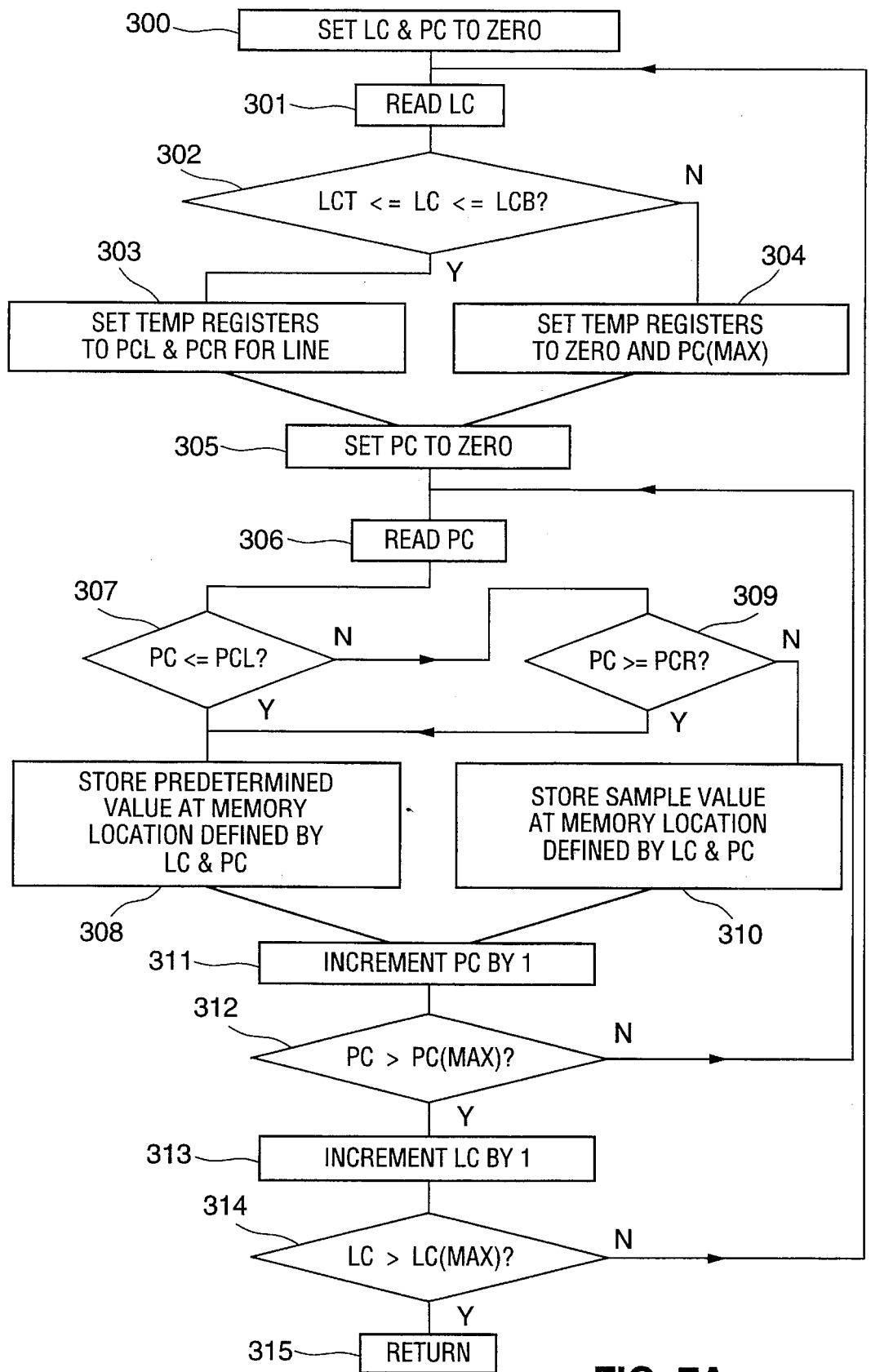
FIG. 7A is a flow chart showing the main routine by which blanking is applied to the external area in a video-based fibre-optic imaging system according to the invention.

To apply different processing to the image and the external area, the DSP 153 processes each frame of the digital video signal received from the analog to digital converter 183 using the routine shown in FIG. 7A. In step 300, the digital signal processor initializes a line counter LC and a pixel counter PC to zero. The line counter and the pixel counter can be registers in the DSP, or can be memory locations in the RAM 157. Also in this step, the DSP resets the CCD array 151 (FIG. 3).

In step 301, the DSP 153 reads the line number from the line counter, and in step 302, the DSP determines whether the line is a boundary line. In the preferred embodiment, the DSP makes this determination by using steps similar to steps 307 and 309, to be described below, to test whether the line number lies between the line numbers of the top boundary line and the bottom boundary line. These values are found in the additional number pair in the image boundary table stored in the RAM 157.

If the line is a boundary line, at step 303, the DSP copies the first of the number pair for the line (the pixel number PCL of the left boundary pixel) from the image boundary table to a first register, and the second of the number pair for the line (the pixel number PCR of the right boundary pixel) from the image boundary table to a second register.

If the line is not a boundary line, execution passes to step 304, where the DSP 153 sets value in the first register to zero, and the value in the second register to a number equal to the maximum number of pixels PC(MAX) in a line, e.g., to 783 (the first pixel is pixel 0).

At step 305, the DSP 153 sets a pixel counter PC to zero. At step 306, the DSP reads the pixel number from the pixel counter. At step 307, the DSP tests whether the value in the pixel counter is less than or equal to the value in the first register. If the result is YES, indicating that the pixel is in the external area, execution passes to step 308, where the DSP ignores the sample value for the pixel received from the analog-to-digital converter 183, and instead stores a predetermined value in the frame store 155 at the memory location defined by the current values of the line counter and the pixel counter. The predetermined value, which, for example, is a value corresponding to black level, will be described in detail below. Execution then passes to step 311.

If the result at step 307 is NO, execution passes to step 309, where the DSP 153 tests whether the value in the pixel counter is greater than or equal to the value in the second register. If the result is YES, this indicates that the pixel is in the external area, and execution passes to step 308, where the DSP ignores the sample value for the pixel received from the analog-to-digital converter 183, and instead stores a predetermined value in the frame store 155 at the memory location indicated by the current values of the line counter and the pixel counter, as described above.

If the result in step 309 is NO, the pixel number is greater than the pixel number of the left pixel number and less than the pixel number of the right pixel number, which indicates that the pixel is a pixel on which the image falls. Accordingly, execution passes to step 310, where the DSP 153 stores the sample value for the pixel received from the analog-to-digital converter 183 (FIG. 3) at the memory location in the frame store 155 indicated by the current values of the line counter and the pixel counter.

At step 311, the DSP increments the value of the pixel counter by 1, and at step 312, tests whether value in the pixel counter is greater than the maximum pixel number PC(MAX), e.g., >783. If the result is NO, indicating that the new pixel number corresponds to a pixel on the line, execution returns to step 306, where the next pixel is processed. Otherwise, and the result is YES, execution advances to step 313, at which the DSP increments the value in the line counter by 1, and tests, at step 314, whether the value in the line counter is greater than the maximum line number LC(MAX), e.g., >491. If the result is NO, execution returns to step 301 to process the next line. Otherwise, and the result is YES, indicating that all the lines in the frame have been processed, execution advances to step 315, which returns execution to the main routine.

A result similar to that achieved by the processing just described may be provided by feeding all the samples in one frame of the digital video signal from the analog-to-digital converter 183 into the frame store 155 without processing them, and then applying processing similar to that just described when the DSP 153 reads the stored samples out of the frame store. In this case, the DSP generates the digital video output signal directly from the sample value in the frame store for each pixel on which the image falls. For each pixel in the external area, the DSP ignores the stored sample value for the pixel, and instead generates the appropriate predetermined value, and from it, the digital video output signal.

As a further alternative, the above processing be carried out in real time to generate the digital video output signal from the digital video signal from the analog-to-digital converter 183 without the need for the frame store 155.

Black Level External Area

In step 308 of the routine shown in FIG. 7A, the DSP 153 stores a predetermined value in the in the frame store 155 at the memory location corresponding to each pixel in the external area. In this embodiment, the predetermined value is a value corresponding to black level.

Setting the Luminance and/or Hue of the External Area with Optional Spatial Variation In step 308 of the routine shown in FIG. 7A, the DSP 153 stores a predetermined value in the in the frame store 155 at the memory location corresponding to each pixel in the external area. In this embodiment, the predetermined value is a value corresponding to a predetermined, or user selectable, luminance level and, optionally, hue.

A spatial variation, i.e., a position-dependent variation, such as a radial variation, may be imposed on the predetermined luminance and hue of the external area. For example, the luminance can be made to fade progressively to black level between the periphery of the image and the edge of the frame. Alternatively or additionally, the radial variation can include one or more step functions to provide a centered or offset shadow or color contrast perimeter around the image.

Figure 7B:
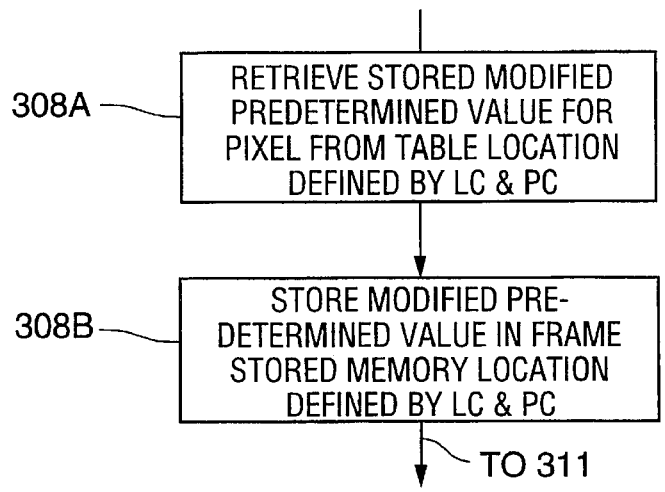
FIG. 7B is a flow chart showing how step 308 of the routine shown in FIG. 7A is modified to impose a radial variation on the external area.

As an example of providing a spatial variation, providing a radial variation will now be described. To provide a radial variation of the predetermined luminance and hue of the external area, the DSP executes a routine to calculate and store in the RAM 157 a modified predetermined value for each external area pixel when the user selects or changes the radial variation. The desired radial variation is defined by an algorithm or a look-up table that relates luminance level and hue in the external area to radial distance from the center of the active area or radial distance from the boundary of the image. Then, at step 308 in the routine shown in FIG. 7A, the DSP executes the modified processing shown in FIG. 7B. In step 308A, the DSP retrieves the stored modified predetermined value for the external area pixel from the address in a modified predetermined value table stored in the RAM 157, and at step 308B, the DSP stores the modified predetermined value in the frame store 155 at the memory location corresponding to the pixel.

To generate a modified predetermined value for each external area pixel, the DSP 153 first looks up the line number and pixel number of the center of the image calculated by the set-up routine. Then, the DSP calculates the distance of each pixel in the external area from the center of the image, and, from this, the radial distance of each pixel from the boundary of the image. From this latter distance, the DSP determines a modifying factor for the pixel using the algorithm or look-up table. The DSP then multiplies the predetermined value by the modifying factor to calculate the modified predetermined value for the pixel. As an alternative to multiplying the predetermined value by the modifying factor, the DSP 153 can calculated the modified predetermined value by performing some other operation, such as adding, scaling, or level shifting, between the predetermined value and the modifying factor.

The DSP 153 stores the modified predetermined value thus calculated in a table of modified predetermined values in the RAM 157. The table is preferably in the form of a matrix so that each modified predetermined value is stored at an address defined by the line number and pixel number of the pixel.

If the desired spatial variation is not radial, the table of modified predetermined values for each pixel in the external area would be provided as a look-up table or would be generated from a function defining the spatial variation.

In all of the above examples, the table of modified predetermined values for the external area could be generated by executing a known graphics program. This could be done in advance, and the results stored in the frame store 155, or the graphics program could be executed in real time.

Adaptive External Area Luminance and/or Hue

In this embodiment, the DSP 153 optimizes the observer's perception of the image by varying the luminance and hue of the external area in response to the luminance and hue of the image. To achieve this, the DSP first determines the luminance level and hue of the image. It is preferable that this determination be made over a relatively long time to make changes in the external area resulting from changes in luminance and hue the image imperceptible, and hence not distracting. The DSP can determine an average luminance level of the image, or a peak luminance level, or some other form of luminance level. The DSP can also determine a predominant hue of the image.

From the luminance level and hue of the image, the DSP 153 then determines a luminance and hue for the external area. The DSP can derive the luminance and hue of the external area from that of the image by using a suitable algorithm, or a look-up table, to provide an adaptively-determined value or set of adaptively-determined values corresponding to the determined luminance and hue of the external area. Then, in step 308 of the routine shown in FIG. 7A, the DSP stores the adaptively-determined value as the predetermined value in the frame store 155 at each memory location corresponding to an external area pixel.

A spatial variation, i.e., a position-dependent variation, such as a radial variation, similar to that described above, can also be imposed on the adaptively-determined luminance and hue of the external area in this embodiment. For example, to achieve a radial variation, the DSP executes a routine to calculate radial modifying factor for each external area pixel, as described above. The radial modifying factors are stored in a table according to the line number and pixel number of the pixels to which they relate. Each time the DSP calculates an adaptively-determined value corresponding to the determined luminance and hue of the external area, it multiplies, or otherwise modifies, as described above, the adaptively-determined value by the radial modifying factor for each external area pixel, and stores the resulting modified adaptively-determined value at an address in a second table defined by the line number and pixel number of the pixel. Then, in step 308 of the routine shown in FIG. 7A, the DSP carries out processing similar to that shown in FIG. 7B, and retrieves the modified adaptively-determined value for each external area pixel from the second table, and stores it as the predetermined value for the external area pixel in the frame store 155 at the memory location corresponding to the pixel.

DISPLAY FRAME LAYOUT

In known video display systems for small-diameter endoscopes, the location of the image 52 in the frame displayed on the monitor 40 corresponds to the location of the image on the image sensor in the remote head in the camera. Thus, the image is nominally displayed in the center of the monitor screen. This layout requires the use of external equipment, such as a video switcher, to be able to display auxiliary information, such as patient monitoring data, or video system parameters, in the external area surrounding the image, or to be able to display multiple endoscope images on the same monitor.

The video-based fibre-optic imaging system according to the invention enables the image to be placed in a location on the monitor screen that is more useful than the center. The location of the image on the screen may be predetermined by the manufacturer, or selected by the user. For example, the image may be displaced to one side so that a larger continuous area of the screen is available for displaying auxiliary data. This would also allow more than one image to be displayed on one screen.

The image relocation feature allows the image to be displayed in the chosen location on the monitor screen despite random variations in the position of the image on the image sensor due to mechanical tolerances in the optical assembly. Displaying the image in the same place on the monitor screen can, over time, cause a sharply-delineated burn area on the screen. The boundary of the burn area becomes noticeable if the diameter of the image increases, or if the position of the image on the screen changes. The image relocation feature can randomly vary the location of the image on the screen by small amounts about the chosen location. This reduces the sharpness of the burn area and makes the burn area less noticeable.

Image Relocation

In a conventional video-based fibre-optic imaging system, the analog output from the CCD array is displayed on the monitor screen. The output of each pixel of the CCD array is displayed at a fixed location on the monitor screen. In the video-based fibre-optic imaging system according to the invention as so far described, there is a similar fixed relationship between the CCD array and the monitor screen. Samples from the CCD array are written into and read out of the frame store 155 sequentially, starting with pixel number zero of line number zero, proceeding via pixel number 783 in line number zero, and ending at pixel number 783 of line number 491. If the monitor requires an interlaced video signal, the pixels for the odd lines are read before the pixels for the even lines in the above sequential reading or writing operation.

In an imaging system with a relocation facility according to the invention, the user may use an image offset control to change the position of the image on the monitor screen. In response to the image offset control, the digital signal processor (DSP) 153 changes the position of the image on the screen by writing the sample values from the image into or reading the sample values from the image out of the frame store 155 in an altered sequential relationship to the predetermined values for the external area.

Figure 8:
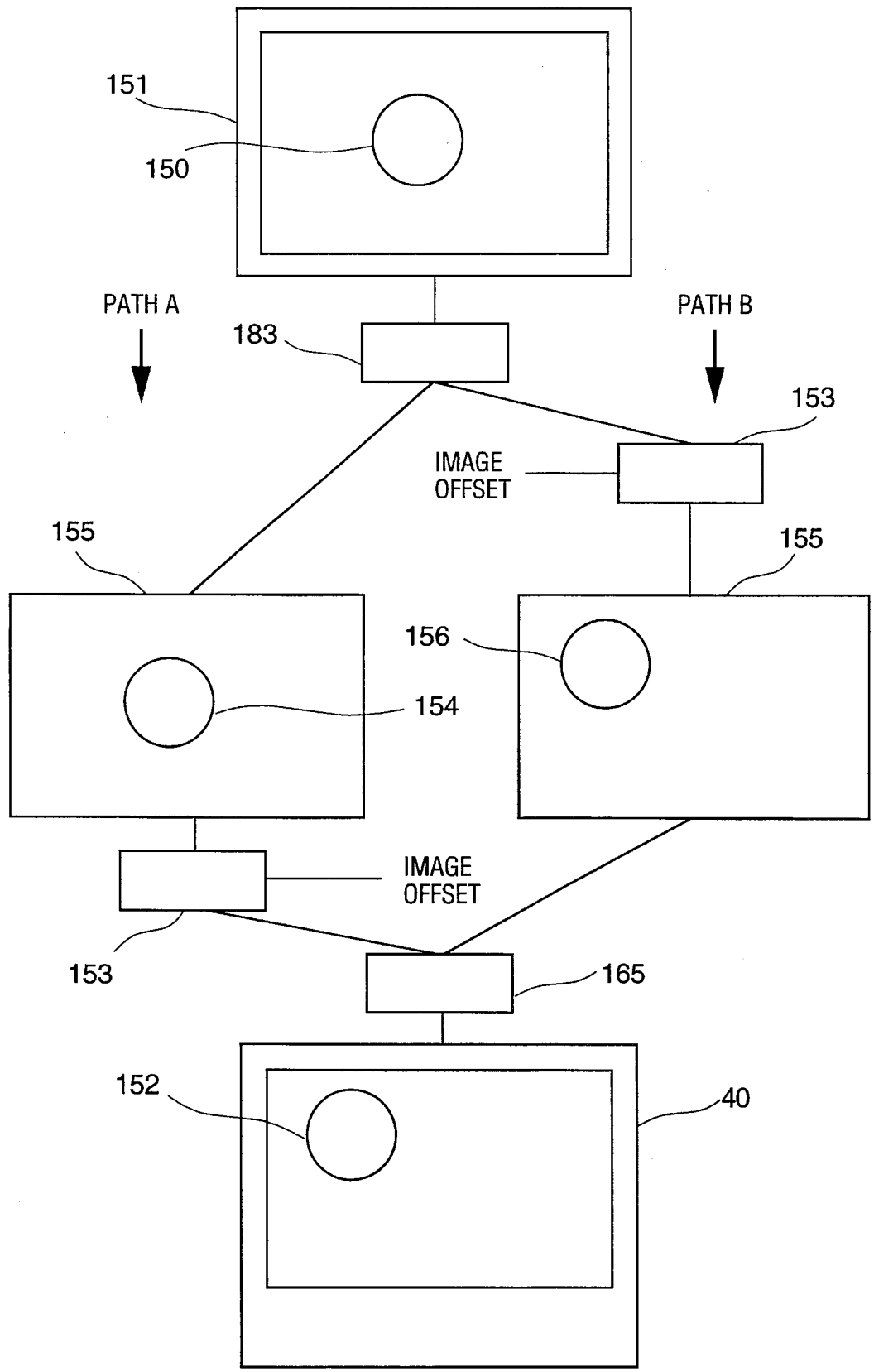
FIG. 8 is a flow chart showing two alternative methods by which the position of the image on the screen may be changed in a video-based fibre-optic imaging system according to the invention.

FIG. 8 shows flow charts of two alternative ways of displaying the image formed by the endoscope on the image sensor in the remote head of the camera with the image offset from the center of the screen of the monitor 40. Components in FIG. 8 that are the same as those shown in FIG. 2 have the same reference numbers. FIG. 8 shows an example in which the image displaced from the center of the screen upwards by about 100 lines and to the left by about 200 pixels.

In common to both paths, the image is formed on the CCD array 151. The location of the pixels in the CCD array on which the image falls is indicated by the hatched area 150. The pixel samples from the CCD array 151 are digitized by the analog-to-digital converter 183. Also common to both paths, a digital video signal is converted to an analog video signal by the digital-to-analog converter 165, and the resulting analog video signal is displayed on the monitor 40. The location of the image on the monitor screen is indicated by the hatched area 152.

In path A, the samples from the analog-to-digital converter 183 are stored in sequence in corresponding memory positions in the frame store 155. The location in the frame store of the samples corresponding to the image is shown as the hatched area 154. This location corresponds to the location of the pixels in the CCD array 151 on which the image falls. The DSP 153 then reads the samples corresponding to the image out of the frame store 155 out of sequence in response to the image offset input. The DSP generates a predetermined value instead of using the sample values for the external area, as described above. This causes the location of the image in the resulting digital video signal to be offset, so that when the digital video signal is converted into an analog signal and displayed on the monitor 40, the image is in the offset position shown.

In path B, the DSP 153 stores the samples from the analog-to-digital converter 183 in the frame store 155 out of sequence in response to the image offset input. This causes the samples corresponding to the image to be located in the frame store in the hatched area 156, which corresponds to the location on the monitor screen in which the image will be displayed. The DSP stores a predetermined value in the rest of the frame store, as described above. The DSP then reads the samples out of the frame store 155 in sequence, so that when the resulting digital video signal is converted into an analog video signal and displayed on the monitor 40, the image is in the offset position shown.

The position of the image on the screen is determined by an image offset, which consists of a line offset and a pixel offset defining the offset between the center of the image and the center of the screen. Preferably, the image offset is preferably zero when the image is centered in the display. During the set-up routine, the image offset is temporarily set to zero so that memory locations in the frame store 155 are correlated with pixel locations in the CCD array 151. The DSP keeps two memory spaces in the RAM 157 which the line offset and the pixel offset defining the image offset are stored.

Normally, the image offset would be predetermined by the manufacturer. Alternatively, plural image offsets would be provided corresponding to different positions of the image on the screen. The user would then use the control panel 187 to select one of the image offsets corresponding to the desired position of the image on the screen.

If the user is to be provided with full control of the position of the image on the screen, the control panel 187 (FIG. 3) would include an image position control for this purpose. The image position control could include a joystick, or four direction control keys (left, right, up, and down) in a conventional inverted 'F' arrangement, or some other arrangement. The main program running on the DSP would regularly invoke a control panel routine that would include a section that checks the direction control keys, and in response thereto, gradually changes (i.e., increments or decrements) the values of the image offset.

The DSP 153 would also monitor the line offset and pixel offset, and would stop changing them when to change them further would result in part of the image being positioned off the screen. The DSP would add to and subtract from the line offset a number corresponding to the radius of the image in lines. The DSP would test whether the results were within the range of the line numbers, e.g., <0 and >491, and would stop changing the line offset if the result went out of this range. Similarly, the DSP would add to and subtract from the pixel offset a number corresponding to the radius of the image in pixels. The DSP would test whether the results were within the range of pixel numbers, e.g., <0 and >783, and would stop changing the pixel offset if the result went out of this range.

The image offset controls, operating in conjunction with the image offset processing, would allow the user to change the position of the image on the display. Alternatively, the user could enter image offset amounts (line offset and pixel offset) from a keyboard or key pad. The control panel routine, after testing the range of the input offset amounts, would then store the offset amounts in the image offset memory locations in the RAM 157.

Figure 7C:
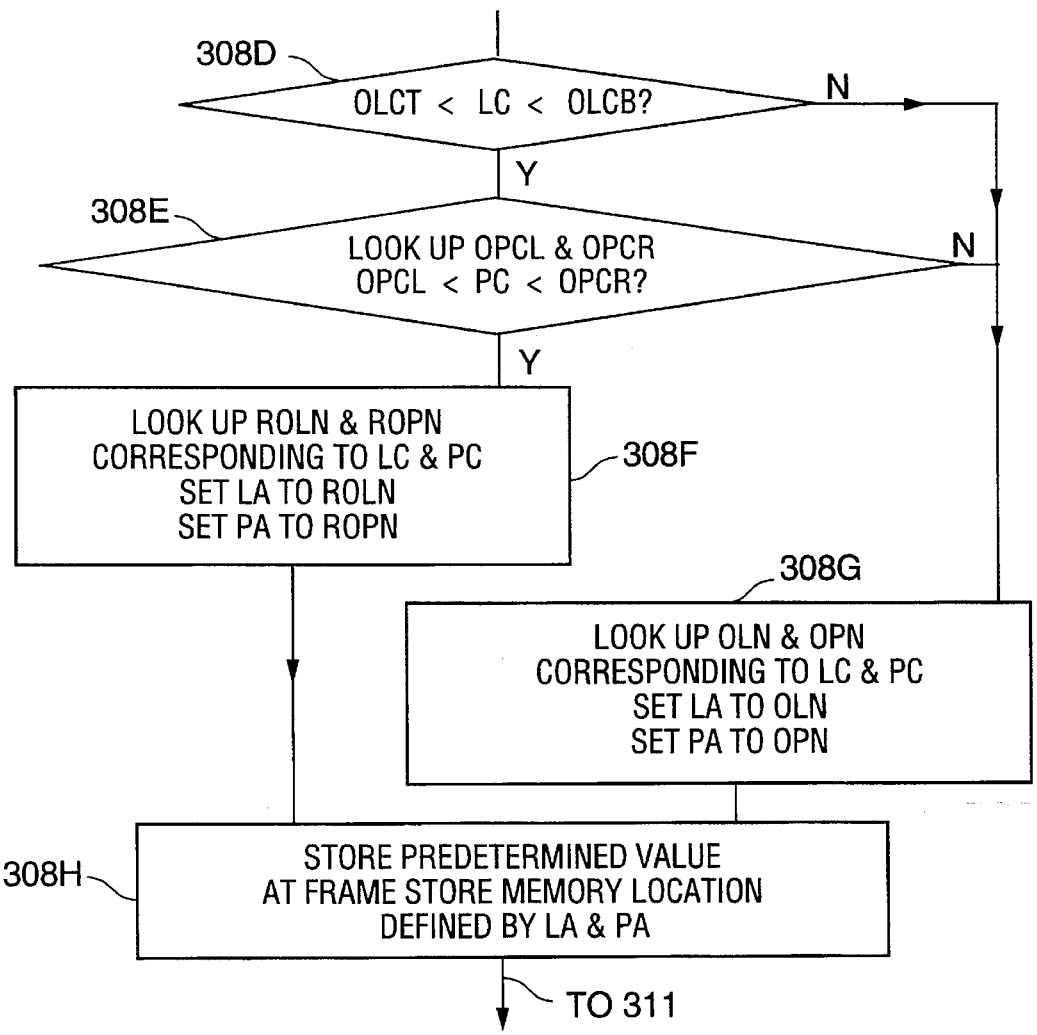
FIG. 7C is a flow chart showing how step 308 of the routine shown in FIG. 7A is modified to relocate the image on the screen.

In an imaging system with image relocation according to the invention, the routine shown in FIG. 7A is used to write sample values or predetermined values into the frame store 155, but steps 308 and 310 are modified as shown in FIGS. 7C and 7D, which will be described in detail below. The effect of the modified processing is to store the sample values corresponding to the image in offset locations in the frame store 155, and to store a predetermined value in each location in the frame store in which a sample value corresponding to the image would have been stored if the image had not been offset.

For use by the routines shown in FIGS. 7C and 7D, the DSP 153 executes a routine that constructs an offset boundary section in the image boundary table. The offset boundary section is calculated by adding the line offset and the pixel offset to the line numbers and pixel numbers, respectively, in the image boundary table. Thus, the offset boundary section includes, for each line in the image boundary table, an offset line number, an offset left pixel number and an offset right pixel number. Additionally, the offset boundary section includes the line number of the offset top line and the line number of the offset bottom line. The offset boundary section defines the boundary of the image in its offset position in terms of the offset top line number and the offset bottom line number and, for each line between the offset top line and the offset bottom line, the offset left pixel number and the offset right pixel number.

The DSP 153 also constructs two additional tables. A offset line number table includes two values for each line, an offset line number, which is the sum of the line number and the line offset, and reverse offset line number, which will be described below. A offset pixel number table includes two values for each pixel, an offset pixel number, which is the sum of the pixel number and the pixel offset, and a reverse offset pixel number, which will be described below. As an alternative to constructing the tables described, the DSP could calculate offset values and reverse offset values when needed during the routines.

To prevent data overwrites, the memory locations that would normally be occupied by sample values from the image would be set to a predetermined value in a mirror order using memory location addresses determined by the reverse offset line number table and the reverse offset pixel number table. To construct the reverse offset line number table, for each line, the DSP 153 subtracts the line number from the sum of the line offset and twice the line number of the center of the image. The DSP determines the reverse pixel line number similarly.

If the image position is user-adjustable, the DSP 153 must monitor the image offset values, and carry out the above processing each time one of the offset values changes. Otherwise, the processing need only be carded out after each time the set-up routine described above is executed. In an embodiment in which the image position were set to a predetermined position, or to a selected one of predetermined positions, and the image boundary is predetermined, there is no need for this processing, and the offset boundary section, the offset line number table, and the offset pixel number table can be predetermined and stored in a suitable memory, such as the ROM 177.

When the image is offset, at steps 308 and 310 of the routine shown in FIG. 7A, the DSP 153 performs the modified processing shown in FIG. 7C and 7D, respectively. The DSP performs the modified processing of step 308 shown in FIG. 7C when the line counter and the pixel counter indicate that the sample value from the digital to analog converter 183 corresponds to the external area. At step 308D, the DSP 153 tests whether the value of the line counter LC is within the range between the offset top line number and the offset bottom line number stored in the offset boundary table. If the result is NO, execution passes to step 308G, which will be described below. Otherwise, and the result is YES, indicating that the line is in the range of lines on which the offset image is located, execution passes to step 308E.

At step 308E, the DSP 153 looks up the offset left pixel number and the offset right pixel number from the line in the offset boundary section indicated by the line counter. The DSP tests whether the value of the pixel counter PC is within the range between the offset left pixel number and the offset right pixel number. If the result is NO, execution passes to step 308G, which will be described below. Otherwise, and the result is YES, indicating that the address indicated by the line counter and the pixel counter defines a memory location in the frame store that is or will be occupied by a sample value from the image, execution passes to step 308F.

At step 308F, the DSP 153 determines the address in the frame store at which the predetermined value will be stored by looking up the line offset table the reverse offset line number corresponding to the line number and looking up in the pixel offset table the reverse offset pixel number. The DSP sets a line address LA and a pixel address PA in a storage address register to these values. Execution then passes to step 308H, where the DSP stores the predetermined value in the frame store 155 at the memory location indicated by the line address and the pixel address in storage address register, thus completing the modified processing of step 308. The DSP stores the predetermined value at an address in the frame store indicated by the reverse offset line number and reverse offset pixel number.

A NO result at either of steps 308D or 308E indicates that the address indicated by the line counter and the pixel counter defines a memory location in the frame store that is not or will not be occupied by a sample value from the image, and execution passes to step 308G. At step 308G, the DSP sets the line address LA and the pixel address PA of the storage address register to the current value of the line counter and the pixel counter, respectively. Then, in step 308H, the DSP stores the predetermined value in the frame store 155 at the memory location indicated by the line address and the pixel address in the storage address register, thus completing the modified processing of step 308. At step 308H, the DSP stores the predetermined value at its "normal" address in the frame store, i.e., at the location indicated by the line counter and the pixel counter.

Step 310 is modified as shown in FIG. 7D. In step 310A, the DSP 153 determines the address in the frame store at which the sample value will be stored by looking up in the line offset table the offset line number corresponding to the line number and looking up in the pixel offset table the offset pixel number corresponding to the pixel number. Then, in step 310B, the DSP stores the sample value in the frame store 155 at the address defined by the offset line number and the offset pixel number. Thus, the sample values for the image are stored at offset memory locations in the frame store 155.

Figure 9A:
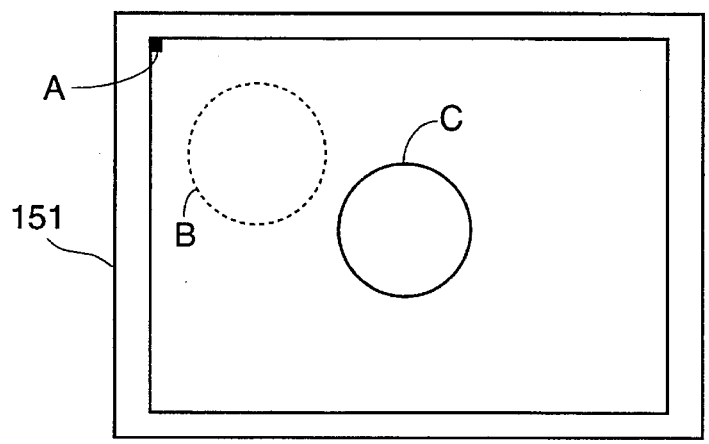
FIGS. 9A through 9C illustrate relocating the image on the screen in a video-based fibre-optic imaging system according to the invention.
Figure 9B:
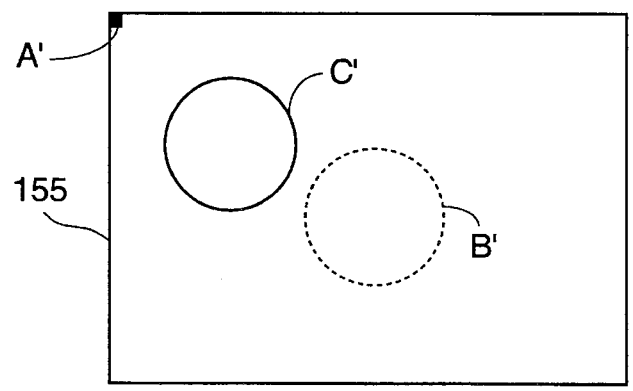
Figure 9C:
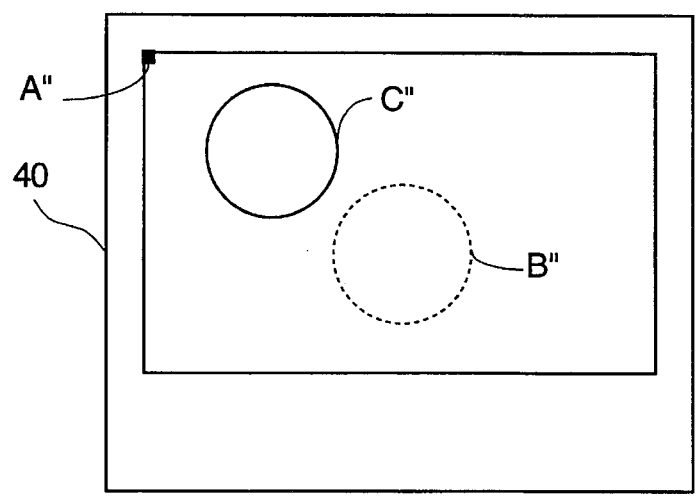

An example of the operation of image relocation is shown in FIGS. 9A through 9C. In this example, image is centered on the CCD array 151, i.e., the center of the image is at pixel 391 on line 245. The image has a radius of 100 lines or pixels. The top boundary line is line 145, the bottom boundary line is line 345. The line offset is −100 lines, and the pixel offset is −200 pixels. Hence the offset center of the image is at pixel 191 on line 145, the offset top line is line 45, and the offset bottom line is line 245.

In FIG. 9A, the pixel A on the CCD array 151 is on the line with a line number of zero, and has a pixel number of zero. The pixel is in the external area, and hence the modified processing of step 308 shown in FIG. 7C is applied. At step 308D, it is determined that the pixel A is outside the range of offset lines, so execution passes to step 308G, where the storage address is set to the current values of the line counter and the pixel counter, i.e., 0,0. Consequently, at step 308H, the DSP stores the predetermined value in the frame store 155 at the "normal" memory location defined by the line number and the pixel number, i.e., at the memory location 0,0, marked A' in FIG. 9B. When the frame store 155 is sequentially read by the DSP, and the resulting video signal is displayed on the monitor 40, the predetermined value stored in the memory location A' in the frame store is displayed at the location A" on the screen, as shown in FIG. 9C.

The pixel B shown in FIG. 9A is on the line with a line number of 145, and has a pixel number of 92. The pixel is in the external area, so the modified processing of step 308 is applied. At step 308D, it is determined that the line on which pixel B is located is within the range of offset lines, so execution passes to step 308E. At step 308E, the DSP determines that the offset left and right pixel numbers of the offset line corresponding to line 145 are 91 and 291, respectively. Thus, the pixel 92 is in this range, so execution passes to step 308E, where the DSP looks up the reverse offset line number and the reverse offset pixel number for pixel B. The reverse offset line number is (((2×245)+(−100))−145)=245. The reverse offset pixel number is (((2×391)+(−200))−92=490.

Execution passes to step 308H where the line address and the pixel address are set to the current values of the reverse offset line number and the reverse offset pixel number determined in step 308G. i.e., 245, 490. Consequently, in step 308H, the DSP stores the predetermined value at the offset memory location defined by the reverse offset line number and the reverse offset pixel number, i.e., at the memory location 245, 490, marked B' in FIG. 9B.

When the frame store 155 is sequentially read by the DSP, and the resulting video signal is displayed on the monitor 40, the predetermined value stored in the memory location B' in the frame store is displayed at the location B" on the screen, as shown in FIG. 9C.

The pixel C shown in FIG. 9A is on the periphery of the image, on the line with a line number of 145, and has a pixel number of 391. The pixel is in the image, so the modified processing of step 310 is applied. At step 310A, the DSP looks up the offset line number and the offset pixel number for pixel C. The offset line number is (145+(−100))=45. The offset pixel number is (391+(−200))=191. Execution passes to step 310B, where the DSP 153 stores the sample value in the frame store 155 at the memory location defined by the offset line number and the offset pixel number, i.e., at the memory location 45, 191, marked C' in FIG. 9B.

When the frame store 155 is sequentially read by the DSP, and the resulting video signal is displayed on the monitor 40, the predetermined value stored in the memory location C' in the frame store is displayed at the location C" on the screen, as shown in FIG. 9C. It will be noted that the sample value for the pixel C is stored in the memory location C' at which the predetermined value for the pixel B would have been stored if the image were not offset.

As mentioned above, the above result may alternatively be provided by the DSP 153 feeding all the samples provided by the analog-to-digital converter 183 into the frame store 155 without processing them, and then applying processing similar to that just described when the it reads the stored samples out of the frame store. In this case, the DSP reads the memory locations in the frame store in a sequence determined by the line counter and the pixel counter until a pixel corresponding to the left boundary of the offset image is reached, at which point, the line counter and the pixel counter are incremented by the image offset values so that the sample values of the image, starting at the left boundary are read. This process continues until the pixel counter reaches the pixel number of the offset right boundary, at which point the line counter and pixel counter are decremented by the offset values. This process is repeated on each line on which the offset image falls. For each pixel on which the offset image falls, the DSP generates the digital video output signal directly from the sample value of the pixel stored in the image area of the frame store 155. For each pixel in the external area, the DSP generates the predetermined value and generates the digital video output signal directly from the predetermined value.

Screen Burn Reduction

The video-based endoscopic imaging system according to the invention can reduce the sharpness of the edge of the burn mark on the monitor scream that would otherwise result from a sharp-edged image being located in the same place on the screen. The imaging system reduces the sharpness of the edge of the burn mark by slowly changing the position of the image on the screen. The change in position is small, and the position is changed slowly, so as to be imperceptible to the user. This feature is important because the image relocation feature just described eliminates the random variations in the position of the image on the screen that occur when there are mechanical tolerances in the optical assembly and the image appears in the same position on the monitor screen as on the image sensor.

The system reduces the sharpness of the edge of the burn mark by a routine that slowly and progressively changes the line number offset and the pixel number offset stored in the RAM 157. Each time after it changes the offset values, the DSP recalculates the offset section of the image boundary table, the offset line number table and the offset pixel number table. Then, the DSP uses the recalculated data in the routine shown in FIG. 7A, in which steps 308 and 310 are modified as shown in FIG. 7C and 7D, respectively. This results in the image being displayed in a slightly different position on the screen.

To vary the offset values, the DSP could, for example, store in the RAM 157 the image offset values defining the present position of the image. The DSP also stores the image offset values of the nominal position of the image in the image offset locations in the RAM 157, as discussed above. Finally, the DSP could store image offset values defining a new position of the image.

The DSP 153 could generate two random numbers in the range of −n to +n, where n is the maximum desired excursion of the image from its nominal position. The DSP would add the random numbers to the image offset values defining the nominal position of the image, to determine a new position for the image. The DSP would then determine a vector between the present position of the image and the new position. The DSP would then slowly increment or decrement, in steps of 1, the offset values defining the present position of the image to move the image along the calculated vector to the new position.

After the image had been in the new position for a predetermined time, the DSP would generate another pair of random numbers to define the next new position for the image. The random numbers can be weighted, if desired, so that the image spends more time close to its nominal position.

Although the application has described illustrative embodiments of the invention in detail, it is to be understood that the invention is not limited to the precise embodiments described, and that various modifications may be practiced within the scope of the invention defined by the appended claims.

I claim:

1. A method of deriving an output video signal by processing an input video signal generated by an image sensor on which an image of a fibre-optic imaging bundle is formed by an image-forming apparatus of which the fibre-optic imaging bundle is a part, the image of the fibre-optic imaging bundle being formed on only a part of the image sensor to mitigate pixellation artifacts resulting from the optical fibres of the fibre-optic imaging bundle, the method comprising steps of:

receiving the input video signal, the input video signal including plural frames, each of the frames having a frame structure, each of the frames including an image portion generated by the part of the image sensor on which the image of the fibre-optic imaging bundle is formed, and an external portion generated by the part of the image sensor on which the image is not formed;

automatically identifying the external portion of the input video signal;

synthesizing, in response to the identifying step, a synthesized external signal portion corresponding to the external portion of the input video signal; and generating frames of the output video signal by replacing the external portion of each of the frames of the input video signal with the synthesized external signal portion synthesized in the synthesizing step to provide a respective one of the frames of the output video signal with the same frame structure as the frames of the input video signal, wherein, in the step of synthesizing a synthesized external signal portion, the synthesized external signal portion is synthesized to have a predetermined level.

2. The method of claim 1, wherein, in the step of synthesizing a synthesized external signal portion, the synthesized external signal portion is synthesized to have a level corresponding to black level.

3. The method of claim 1, wherein, in the step of synthesizing a synthesized external signal portion, the synthesized external signal portion is synthesized to have a level corresponding to a predetermined luminance and, when the output video signal is a color video signal, to a predetermined hue.

4. The method of claim 1, wherein:
  the step of synthesizing a synthesized external signal portion includes steps of:
  determining at least one of a luminance and a hue of the image portion of the input video signal;
  adaptively determining at least one of an adaptively-determined luminance and an adaptively-determined hue in response to the at least one of the luminance and the hue of the image portion of the input video signal determined in the determining step; and
  generating the synthesized external signal portion with a level corresponding to the at least one of the adaptively-determined luminance and the adaptively-determined hue.

5. The method of claim 3, wherein the step of synthesizing a synthesized external signal portion includes a step of spatially varying at least one of the predetermined luminance and the predetermined hue.

6. The method of claim 5, wherein:
  the image has a center;
  in the step of spatially varying at least one of the predetermined luminance and the predetermined hue, the at least one of the predetermined luminance and the predetermined hue is varied in a radially-varying pattern centered on the image; and
  the step of spatially varying at least one of the predetermined luminance and the predetermined hue includes steps of:
    determining, for each one of plural points in the external portion of the input video signal, a distance of the one of the points from the center of the image, and, and, for each one of the plural points:
      determining a correction factor from the distance of the one of the points and the radially-varying pattern; and
      modifying the level corresponding to the at least one of the predetermined luminance and the predetermined hue according to the correction factor.

7. The method of claim 4, wherein the step of synthesizing a synthesized external signal portion additionally includes a step of spatially varying at least one of the adaptively-determined luminance and the adaptively-determined hue prior to the generating step.

8. The method of claim 7, wherein:
  the image has a center;
  in the step of spatially varying at least one of the predetermined luminance and the predetermined hue, the at least one of the predetermined luminance and the predetermined hue is varied in a radially-varying pattern centered on the image,
  the step of spatially varying at least one of the predetermined luminance and the predetermined hue includes steps of:
    determining, for each one of plural points in the external portion of the input video signal, a distance of the one of the points from the center of the image, and, for each one of the plural points:
      determining a correction factor from the distance of the one of the points and the radially-varying pattern, and
      modifying the level corresponding to the at least one of the adaptively-determined luminance and the adaptively-determined hue according to the correction factor.

9. A method of deriving an output video signal by processing an input video signal generated by an image sensor on which an image of a fibre-optic imaging bundle is formed by an image-forming apparatus of which the fibre-optic imaging bundle is a part, the image of the fibre-optic imaging bundle being formed on only a part of the image sensor to mitigate pixellation artifacts resulting from the optical fibres of the fibre-optic imaging bundle, the method comprising steps of:
  receiving the input video signal, the input video signal including plural frames, each of the frames having a frame structure, each of the frames including an image portion generated by the part of the image sensor on which the image of the fibre-optic imaging bundle is formed, and an external portion generated by the part of the image sensor on which the image is not formed;
  automatically identifying the external portion of the input video signal;
  synthesizing, in response to the identifying step, a synthesized external signal portion corresponding to the external portion of the input video signal; and
  generating frames of the output video signal by replacing the external portion of each of the frames of the input video signal with the synthesized external signal portion synthesized in the synthesizing step to provide a respective one of the frames of the output video signal with the same frame structure as the frames of the input video signal, wherein:
  the image of the fibre-optic imaging bundle is formed in a position on the image sensor,
  the method is for deriving an output video signal wherein, when the output video signal is displayed to provide a picture, the image portion is displayed located in a selected position in the picture, the selected position being different from a position corresponding to the position of the image on the image sensor, and
  in the input video signal, the image portion has a positional relationship to the frames of the input video signal, and wherein:
  the step of generating frames of the output video signal includes a step of transferring the image portion from the frames of the input video signal to the respective frames of the output video signal in a positional relationship to the frames of the output video signal, the transferring step selectively changing the positional relationship of the image portion to the frames of the output video signal relative to the positional relationship of the image portion to the frames of the input video signal.

10. The method of claim 9, wherein the step of transferring the image portion from the frames of the input video signal to the frames of the output video signal includes steps of:
  providing a memory including plural storage locations;
  storing the image portion of the frames of the input video signal and the synthesized external signal portion in the storage locations in the memory corresponding to the positional relationship of the image portion to the frames of the output video signal; and sequentially reading the storage locations in the memory to generate the each of the frames of the output video signal.

11. The method of claim 9, wherein the step of transferring the image portion from the frames of the input video signal to the frames of the output video signal includes steps of:

providing a memory including plural storage locations;

sequentially storing each of the frames of the input video signal into the storage locations in the memory; and reading only the storage locations in the memory wherein the image portion is stored into the respective one of the frames of the output video signal in a sequence corresponding to the positional relationship of the image portion to the frames of the output video signal.

12. The method of claim 9, wherein the method is for deriving the output video signal for display using a display apparatus susceptible to screen burn, and method is for gradually and progressively changing the position in which the image portion of the output video signal is displayed on the display apparatus about the selected position to reduce screen burn on the display apparatus, and the method additionally comprises a step of gradually and progressively changing the positional relationship between the image portion and the frames of the output video signal.

13. The method of claim 10, wherein:

the input video signal additionally includes plural lines each including an image part generated by the part of the image sensor on which the image of the fibre-optic imaging bundle is formed, and an external part generated by the part of the image sensor on which the image is not formed;

in the step of identifying the external portion of the input video signal, the lines including an image part and an external part are identified, and, for each of such lines, a position of a boundary between the image part and the external part is identified; and the step of storing the image portion of the frames of the input video signal and the synthesized external signal portion in storage locations in the memory includes steps of:

reading an image offset indicating the selected position of the image portion in the picture, in response to the image offset and the lines and the boundary positions identified in the identifying step, reserving reserved storage locations corresponding to the positional relationship of the image portion to the frames of the output video signal, and storing each one of the frames of the input video signal in the memory by:

storing the image portion of the one of the frames of the input video signal in the reserved storage locations; and sequentially storing in the storage locations in the memory the Synthesized external image portion synthesized in the synthesizing step in lieu of the external portion of the one of the frames of the input video signal, but, when sequentially storing the synthesized external signal portion would store the synthesized external signal portion in one of the reserved storage locations, storing the synthesized external signal portion in one of the storage locations in which the image portion would be stored if the positional relationship of the image portion to the frames the output video signal were the same as the positional relationship of the image portion to the frames of the input video signal.

14. The method of claim 11, wherein:

the input video signal includes plural lines each including an image part generated by the pan of the image sensor on which the image of the fibre-optic imaging bundle is formed, and an external part generated by the part of the image sensor on which the image is not formed;

in the step of identifying the external portion of the video signal, the lines including an image part and an external part are identified, and, for each of such lines, a position of a boundary between the image part and the external part is identified; and the step of transferring the image portion from the frames of the input video signal to the frames of the output video signal additionally includes steps of:

reading an image offset indicating the selected position of the displayed image, in response to the image offset, and the lines and the boundary positions identified in the identifying step, determining positions of the image portion and the synthesized external signal portion in the output video signal, and reading from the storage locations in the memory into the output video signal by:

sequentially reading the storage locations in the memory wherein the image portion is stored into the image portion of the output video signal, and sequentially reading the synthesized external signal portion into the output video signal, but, when sequentially reading the synthesized external signal portion into the output video signal would read the synthesized external signal portion into the image portion of the output video signal, reading the synthesized external signal portion into a part of the output signal into which the image portion would have been read if the positional relationship of image portion to the frames of the output video signal were the same as the positional relationship of the image portion to the frames of the input video signal.

15. The method of claim 12, wherein the step of gradually and progressively changing the positional relationship between the image portion and the frames of the output signal includes steps of:

initializing a current positional relationship to a value indicating a positional relationship between the image portion and a one of the frames of the output video signal corresponding to the selected position of the displayed image portion; and repeating steps of:

determining the current positional relationship, generating a random variation in the current positional relationship, adding the random variation to the current positional relationship to determine a new positional relationship, calculating a vector between the current positional relationship and the new positional relationship, progressively changing the positional relationship between the image portion and the frames of the output video signal along the vector until the positional relationship reaches the new positional relationship, and setting the current positional relationship to the new positional relationship.

\* \* \* \* \*